(12) United States Patent
Buchsbaum et al.

(10) Patent No.: US 8,703,712 B2
(45) Date of Patent: Apr. 22, 2014

(54) TARGETING CANCER STEM CELLS WITH DR5 AGONISTS

(75) Inventors: Donald J. Buchsbaum, Alabaster, AL (US); Albert F. Lobuglio, Birmingham, AL (US); Tong Zhou, Birmingham, AL (US); Kimberly Foreman, Clarendon Hills, IL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/634,401

(22) PCT Filed: Mar. 18, 2011

(86) PCT No.: PCT/US2011/029081
§ 371 (c)(1),
(2), (4) Date: Sep. 12, 2012

(87) PCT Pub. No.: WO2011/116344
PCT Pub. Date: Sep. 22, 2011

(65) Prior Publication Data
US 2013/0004521 A1    Jan. 3, 2013

(51) Int. Cl.
*A61K 39/00* (2006.01)
*A61P 35/00* (2006.01)
*A61K 39/395* (2006.01)
*C12N 5/095* (2010.01)
*C07K 16/30* (2006.01)

(52) U.S. Cl.
USPC ............ 514/18.9; 424/174.1; 424/130.1; 514/19.4; 435/330; 630/388.8

(58) Field of Classification Search
None
See application file for complete search history.

(56) References Cited

U.S. PATENT DOCUMENTS

| | | | |
|---|---|---|---|
| 5,919,912 A * | 7/1999 | Korneluk et al. | 530/389.2 |
| 6,313,269 B1 | 11/2001 | Deen et al. | |
| 6,417,328 B2 | 7/2002 | Alnemri | |
| 6,756,196 B2 | 6/2004 | Bertin | |
| 7,279,160 B2 * | 10/2007 | Zhou et al. | 424/143.1 |
| 2008/0253966 A1 * | 10/2008 | Bonavida et al. | 424/9.1 |

FOREIGN PATENT DOCUMENTS

| | | |
|---|---|---|
| WO | 98/32856 A1 | 7/1998 |
| WO | 98/35986 A1 | 8/1998 |
| WO | 98/41629 A2 | 9/1998 |
| WO | 98/46642 A1 | 10/1998 |
| WO | 99/02653 A1 | 1/1999 |
| WO | 99/03992 A1 | 1/1999 |
| WO | 99/09165 A1 | 2/1999 |
| WO | 99/11791 A2 | 3/1999 |
| WO | 99/12963 A2 | 3/1999 |
| WO | 00/66156 A1 | 11/2000 |
| WO | 01/83560 A1 | 11/2001 |
| WO | 03/37913 A2 | 5/2003 |
| WO | 2006/83937 A2 | 8/2006 |
| WO | 2008/073581 A2 | 6/2008 |
| WO | 2011/057099 A2 | 5/2011 |

OTHER PUBLICATIONS

Londono-Joshi et al., Basal-like breast cancer stem cells are sensitive to anti-DR5 mediated cytotoxicity, Breast Cancer Res. Treat. 133: 437-445, 2012.*
Wei et al., Apoptosis resistance can be used in screening the markers of cancer stem cells, Med. Hypot., 67, 1381-1383, 2006.*
Rahman et al. TRAIL Induces apoptosis in triple negative breast cancer cells with a mesenchymal phenotype. Breast Cancer Res. Treat. 113, 217-230, 2009—published on line Feb. 12, 2008.*
Rahman et al., The TRAIL to target therapy of breast cancer, Adv. Cancer Res., 103:43-73 (2009).
Singh et al., Synergistic interactions of chemotherapeutic drugs and tumor necrosis factor-related apoptosis-inducing ligand/Apo-2 ligand on apoptosis and on regression of breast carcinoma in vivo, Cancer Res., 63:5390-400 (2003).
Sprick et al., FADD/MORT1 and caspase-8 are recruited to TRAIL receptors 1 and 2 and are essential for apoptosis mediated by TRAIL receptor 2, Immunity, 12:599-609 (2000).
Straughn et al., Anti-tumor activity of TRA-8 anti-death receptor (DR5) monoclonal antibody in combination with chemotherapy and radiation therapy in a cervical cancer model, Gynecol. Oncol., 101:46-54 (2006).
Suzuki et al., X-linked inhibitor of apoptosis protein (XIAP) inhibits caspase-3 and -7 in distinct modes, J. Biol. Chem., 276:27058-63 (2001).
Thomas et al., TNF-related apoptosis-inducing ligand (TRAIL) induces apoptosis in fas-ligand resistant melanoma cells and mediates CD4 T cell killing of target cells, J. Immunol., 161:2195-20 (1998).
Vogler et al., Targeting XIAP bypasses Bcl-2-mediated resistance to TRAIL and cooperates with TRAIL to suppress pancreatic cancer growth in vitro and in vivo, Cancer Res. 68:7956-65 (2008).
Vucic et al., ML-IAP, a novel inhibitor of apoptosis that is preferentially expressed in human melanomas, Curr. Biol. 10:1359-66 (2000).
Vucic et al., The inhibitor of apoptosis proteins as therapeutic targetsin cancer, Clin. Cancer Res., 13:5995-6000 (2007).
Walczak et al., TRAIL-R2: A novel apoptosis-medaiting receptor for TRAIL, EMBO J. 16:5386-97 (1997).
Wen et al., Antileukemic drugs increase death receptor 5 levels and enhance Apo-2L-induced apoptosis of human leukemia cells, Blood, 96:3900-6 (2000).
Wieland et al., Molecular characterization of the DICE1 (DDX26) tumor suprressor gene in lung carcinoma cells, Oncol. Res., 12:491-500 (2001).

(Continued)

*Primary Examiner* — Elly-Gerald Stoica
(74) *Attorney, Agent, or Firm* — Kilpatrick, Townsend & Stockton LLP

(57) ABSTRACT

Provided is a method of determining the level of resistance or sensitivity of cancer stem cells to a death receptor agonist. The method includes detecting the level of IAP in one or more DR5/DDX3/IAP complexes in or from the cancer stem cells. Also provided is a method of killing cancer stem cells in a subject and a method of reducing the risk of cancer recurrence in a subject.

6 Claims, 13 Drawing Sheets

(56) References Cited

OTHER PUBLICATIONS

Wu et al., Enhancement of TRAIL/Apo2L-mediated apoptosis byadriamycin through inducing DR4 and DR5 in renal cell carcinoma cells, Int. J. Cancer, 104:409-17 (2003).
Zhou et al., Immunobiology of tumor necrosis factor receptor superfamily, Immunol. Res., 26:323-36 (2002).
Zhou et al., DDX3 associates with DR5 and negatively regulates apoptosis signal transduction of the death domain, NCI Translation Science Meeting (Nov. 7, 2008) (abstract).
Zhou et al., Anti-DR5 antibody therapy for triple negative breast cancer, NCI Translational Science Meeting (Nov. 5-7, 2009) (abstract).
Burgess, Behind the scenes of a breakthrough, Crossroads: Cancer Center Magazine (Spring 2009).
Cancer: Monoclonal Antibody, Anybody, UAB Magazine: http://www.uab.edu/uabmagazine/breakthroughs/research/cancer (Sep. 2008).
UAB wins $6.4 million nonprofit grant to fight aggressive breast cancer, UAB Media Relations: http://main.uab.edu/Sites/MediaRelations/articles/61698 (Apr. 10, 2009).
Abraham et al., Prevalence of CD44+/CD24–/low cells in breast cancer may not be associated with clinical outcome but may favor distant metastasis, Clin. Cancer Res., 11:1154-1159 (2005).
Ailles et al., Cancer stem cells in solid tumors, Curr. Opin. Biotechnol., 18:460-466 (2007).
Al-Hajj et al., Prospective identification of tumorigenic breast cancer cells, Proc. Natl. Acad. Sci. USA, 100:3983-8 (2003).
Balic et al., Most early disseminated cancer cells detected in bone marrow of breast cancer patients have a putative breast cancer stem cell phenotype,Clin. Cancer Res.,12:5615-21 (2006).
Bonnet et al., Human acute myeloid leukemia is organized as a hierarchy that originates from a primitive hematopoietic cell, Nat. Med., 3:730-7 (1997).
Callahan et al., Notch signaling in mammary development and oncogenesis. J. Mammary Gland Biol. Neoplasia, 9:145-63 (2004).
Campbell et al., Breast tumor heterogeneity: cancer stem cells or clonal evolution? Cell Cycle, 6:2332-2338 (2007).
Capper et al., Stem-cell-like glioma cells are resistant to TRAIL/Apo2L and exhibit down-regulation of caspase-8 by promoter methylation, Acta Neuropathol, 117:445-456 (2009).
Charafe-Jauffret et al., Breast cancer cell lines contain functional cancer stem cells with metastatic capacity and a distinct molecular signature, Cancer Res., 69:1302-1313 (2009).
Charafe-Jauffret et al., Cancer stem cells in breast: current opinion and future challenges, Pathobiology, 75:75-84 (2008).
Dickson et al., High-level JAG1 mRNA and protein predict poor outcome in breast cancer, Mod. Pathol., 20:685-693 (2007).
Dontu, Breast cancer stem cell markers—the rocky road to clinical applications, Breast Cancer Research, 10(5):110 (2008).
Dontu et al., Role of Notch signaling in cell-fate determination of human mammary stem/progenitor cells, Breast Cancer Research, 6:R605-R615 (2004).
Dontu et al., Breast cancer, stem/progenitor cells and the estrogen receptor, Trends Endocrinol. Metab., 15(5):193-197 (2004).
Eyler et al., Survival of the fittest: cancer stem cells in therapeutic resistance and angiogenesis, J. Clin. Oncol., 26:2839-2845 (2008).
Farnie et al., Mammary stem cells and breast cancer—role of Notch signaling, Stem Cell Rev., 3:169-175 (2007).
Fillmore et al., Human breast cancer cell lines contain stem-like cells that self-renew, give rise to phenotypically diverse progeny and survive chemotherapy, Breast Cancer Research, 10:R25 (2008).
Forero-Torres et al., Phase I trial of weekly tigatuzumab, an agonistic humanized monoclonal antibody targeting death receptor 5 (DR5), Cancer Biother Radiopharm., 25(1):13-19 (2010).
Foster et al., Increase of GKLF messenger RNA and protein expression during progression of breast cancer, Cancer Res., 60:6488-6495 (2000).
Ginestier et al., Retinoid signaling regulates breast cancer stem cell differentiation, Cell Cycle, 8:3297-3302 (2009).

Ginestier et al., ALDH1 is a marker of normal and malignant human mammary stem cells and a predictor of poor clinical outcome, Cell Stem Cell, 1(5):555-567 (2007).
Ischenko et al., Cancer stem cells: how can we target them? Curr. Med. Chem., 15(30):3171-3184 (2008).
Jeng, Breast cancer stem cell marker ALDH1 predicts survival rate of breast cancer patients treated with tamoxifen, Proceedings of the 100th Annual Meeting of the American Association of Cancer Research; Apr. 18-22, 2009, Denver, CO; p. Abstract No. 3078 (2009).
Kakarala et al., Implications of the cancer stem-cell hypothesis for breast cancer prevention and therapy, J. Clin. Oncol., 26:2813-2820 (2008).
Katoh, Integrative genomic analyses on HES/HEY family: Notch-independent HES1, HES3 transcription in undifferentiated ES cells, and Notch-dependent HES1, HES5, HEY1, HEY2, HEYL transcription in fetal tissues, adult tissues, or cancer, Int. J. Oncol., 31:461-466 (2007).
Kim et al., High resolution single-photon emission computed tomography and X-ray computed tomography imaging of Tc-99m-labeled anti-DR5 antibody in breast tumor xenografts, Mol. Cancer Ther., 6:866-875 (2007).
Korkaya et al., HER-2, notch, and breast cancer stem cells: targeting an axis of evil, Clin. Cancer Res., 15:1845-1847 (2009).
Korkaya et al., HER2 regulates the mammary stem/progenitor cell population driving tumorigenesis and invasion, Oncogene, 27:6120-6130 (2008).
Lee et al., Molecular dependence of estrogen receptor-negative breast cancer on a notch-survivin signaling axis, Cancer Res., 68:5273-5281 (2008).
Liu et al., Epithelial transformation by KLF4 requires Notch1 but not canonical Notch1 signaling, Cancer Biol.Ther., 8 (19):1840-1851 (2009).
Liu et al., Mammary stem cells, self-renewal pathways, and carcinogenesis, Breast Cancer Research, 7(3):86-95 (2005).
Ashhab et al., Two splicing variants of a new inhibitor of apoptosis gene with different biological properties and tissue distribution pattern, FEBS Lett., 495:56-60 (2001).
Badve et al., Oestrogen-receptor-positive breast cancer: towards bridging histopathological and molecular classifications, J. Clin. Pathol., 62:6-12 (2009).
Bodmer et al., TRAIL receptor-2 signals apoptosis through FADD and caspase, Nat. Cell Biol., 2:241-3 (2000).
Buchsbaum et al., Antitumor efficacy of TRA-8 anti-DR5 monoclonal antibody alone or in combination with chemotherapy and/or radiation therapy in a human breast cancer model, Clin. Cancer Res., 9:3731-41 (2003).
Buchsbaum et al., TRAIL receptor-targeted therapy, Future Oncol., 2:493-508 (2006).
Carey et al., The triple-neagative paradox: primary tumor chemosensitivity of breast cancer subtypes, Clin. Cancer Res., 13:2329-2334 (2007).
Chaudhary et al., Death receptor 5, a new member of the TNFR family, and DR4 induce FADD-dependent apoptosis and activate the Nf-kB pathway, Immunity, 7:821-830 (1997).
Cheang et al., Basal-like breast cancer defined by five biomarkers has superior prognostic value than triple-negative phenotype, Clin. Cancer Res., 14:1368-1376 (2008).
Conforti et al., Discrepancy between triple-negative phenotype and basallike tumor: an immunohistochemical analysis based on 150 'triple-negative' breast cancers, Breast Cancer Res. Treat., 106:S135 (2007).
Crook et al., An apoptosis-inhibiting baculovirus gene with a zinc finger-like motif, J. Virol., 67:2168-2174 (1993).
Delmas et al., Resveratrol-induced apoptosis is associated with Fas redistribution in the rafts and the formation of a death-inducing signaling complex in colon cancer cells, J. Biol. Chem., 278:41482-41490 (2003).
DeRosier et al., TRA-8 anti-DR5 monoclonal antibody and gemcitabine induce apoptosis and inhibit radiologically validated orthotopic pancreatic tumor growth, Mol. Cancer Ther., 6:3198-3207 (2007).

(56) References Cited

OTHER PUBLICATIONS

DeRosier et al., Combination treatment with TRA-8 anti-death receptor-5 antibody and CPT-11 induces tumor regression in an orthotopic model of pancreatic cancer, Clin. Cancer Res., 13:5535-5543 (2007).

Desagher et al., Mitochondria as the central control point of apoptosis, Trends Cell Biol., 10:369-377 (2000).

Deveraux et al., X-linked IAP is a direct inhibitor of cell-death proteases, Nature, 388:300-304 (1997).

Deveraux et al., IAP family proteins-suppressors of apoptosis, Genes Dev., 13:239-252 (1999).

Estes et al., Efficacy of anti-death receptor 5 (DR5) antibody (TRA-8) against primary human ovarian carcinoma using a novel ex vivo tissue slice model, Gynecol. Oncol., 105:291-298 (2007).

Fiveash et al., Enhancement of glioma radiation therapy and chemotherapy response with targeted antibody therapy against death receptor 5, Int. J. Radiat. Oncol. Biol. Phys., 71:507-516 (2008).

Honeth et al., The CD44+/CD24−phenotype is enriched in basal-like tumors, Breast Cancer Research, 10:R53 (2008).

Ichikawa et al., Tumoricidal activity of a novel anti-human DR5 monoclonal antibody without hepatocyte cytotoxicity, Nat. Med., 7:954-960 (2001).

Ichikawa et al., TRAIL-R2 (DR5) mediates apoptosis of synovial fibroblasts in rheumatoid arthritis, J. Immunol., 171:1061-1069 (2003).

Isakoff et al., p63/p73 expression mediates cisplatin sensitivity in a subset of triple-negative primary breast cancer: Implications for a new clinical trial, J. Clin. Oncol., 25:10522 (2007) (abstract).

Johnston et al., Role of the TRAIL/APO2-L death receptors in chlorambucil- and fludarabine-induced apoptosis in chronic lymphocytic leukemia, Oncogene, 22:8356-8369 (2003).

Kaliberov et al., Enhanced apoptosis following treatment with TRA-8 anti-human DR5 monoclonal antibody and overexpression of exogenous Bax in human glioma cells, Gene Ther., 11:658-667 (2004).

Kang et al., Mda-5: an interferon-inducible putative RNA helicase with double-stranded RNA-dependent ATPase activity and melanoma growth-suppressive properties, Proc. Natl. Acad. Sci. USA, 99:637-642 (2002).

Kasof et al., Livin, a novel inhibitor of apoptosis protein family member, J. Biol. Chem., 276:3238-3246 (2001).

Kendrick et al., Anti-tumor activity of the TRA-8 anti-DR5 antibody in combination with cisplatin in an ex vivo human cervical cancer model, Gyencol. Oncol., 108:591-597 (2008).

Kim et al., Early therapy evaluation of combined anti-death receptor 5 antibody and gemcitabne in orthotopic pancreatic tumor xenografts by diffusion-weighted magnetic resonance imaging, Cancer Res., 68:8369-8376 (2008).

Krammer, CD95's deadly mission in the immune system, Nature, 407:789-795 (2000).

Kristensen et al., Gene expression profiling of breast cancer in relation to estrogen receptor status and estrogen-metabolizing enzymes: clinical implications, Clin. Cancer Res., 11:878-883 (2005).

Kuang et al., FADD is required for DR4- and DR5-mediated apoptosis: Lack of TRAIL-induced apoptosis in FADD-deficient mouse embryonic fibroblasts, J. Biol. Chem., 275:25065-25068 (2000).

Lam et al., Comparison of DR5 and Fas expression levels relative to the chemosensitivity of acute lymphoblastic leukemia cell lines, Leuk. Res., 26:503-513 (2002).

Li et al., Inducible resistance of tumor cells to tumor necrosis factor-related apoptosis-inducing ligand receptor 2-mediated apoptosis by generation of a blockade at the death domain function, Cancer Res., 66:8520-8528 (2006).

Li et al., Intrinsic resistance of tumorigenic breast cancer cells to chemotherapy, J. Natl. Cancer Inst., 100:672-679 (2008).

Liedtke et al., Differential response to primary chemotherapy and long-term survival in patients with triple-negative breast cancer, J. Clin. Oncol., 25:10519 (2007) (abstract).

Long et al., TRA-8 (TRAIL-R2 antibody) based combination chemotherapy produces a survival benefit in a pancreatic cancer orthotopic model, J. Surg. Res., 137:167 (2007).

Magnifico et al., Tumor-initiating cells of HER2-positive carcinoma cell lines express the highest oncoprotein levels and are sensitive to trastuzumab, Clin. Cancer Res., 15:2010-2021 (2009).

Mano et al., The 17q12-q21 amplicon: Her2 and topoisomerase and their importance to the biology of solid tumors, Cancer Treat Rev., 33:64-77 (2007).

Naka et al., Effects of tumor necrosis factor-related apoptosis-inducing ligand alone and in combination with chemotherapeutic agents on patients' colon tumors grown in SCID mice, Cancer Res., 62:5800-5806 (2002).

Ohtsuka et al., Bisindolymaleimide VII enhances DR5-mediated apoptosis through the MKK4/JNK/p38 kinase and the mitochondrial pathways, J. Biol. Chem., 277:29294-29303 (2002).

Ohtsuka et al., Synergistic induction of tumor cell apoptosis by death receptor antibody and chemotherapy agent through JNK/p38 and mitochondrial death pathway, Oncogene, 22:2034-2044 (2003).

Oliver et al., Treatment of human colon cancer xenografts with TRA-8 anti-death receptor 5 antibody alone or in combination with CPT-11, Clin. Cancer Res., 14:2180-2189 (2008).

Pan et al., Caspase-9, Bcl-XL, and Apaf-1 form a ternary complex, J. Biol. Chem., 273:5841-5845 (1998).

Rahman et al., TRAIL induces apoptosis in triple-negative breast cancer cells with a mesenchymal phenotype, Breast Cancer Res. Treat, 113:217-230 (2009).

Rajeshkumar et al., Tigatuzumab (CS-1008), a novel humanized DR5 agonist antibody, eradicates pancreas cancer stem cells and results in long term cures, in combination with gemcitabine, in direct pancreas cancer xenografts, Amer. Assoc. Cancer Res. Annual Meeting, Denver, CO (2009).

Rakha et al., Basal-like breast cancer: a critical review, J. Clin. Oncol., 26:2568-2581 (2008).

Saleh et al., A phase I study of CS-1008 (humanized monoclonal antibody targeting death receptor 5 or DR5), administered weekly to patients with advanced solid tumors or lymphomas, J. Clin. Oncol., 26:3537 (2008) (abstract).

Satyamoorthy et al., No longer a molecular black-box-new clues to apoptosis and drug resistance in melanoma, Trends Mol. Med., 7:191-194 (2001).

Scaffidi et al., Two CD95 (Apo-1/Fas) signaling pathways, EMBO J., 17:1675-1687 (1998).

Schneider et al., TRAIL receptors 1 (DR4) and 2 (DR5) signal FADD-dependent apoptosis and activate NF-kB, Immunity, 7:831-836 (1997).

Mani et al., The epithelial-mesenchymal transition generates cells with properties of stem cells, Cell, 133:704-715 (2008).

Miele et al., The cancer stem cell hypothesis, embryonic signaling pathways, and therapeutics: targeting an elusive concept, Am. Soc. Clin. Oncol. Ed. Book, pp. 145-156 (2009).

Miele, Rational targeting of Notch signaling in breast cancer, Expert Rev. Anticancer. Ther., 8:1197-1202 (2008).

Nakshatri et al., Breast cancer stem cells and intrinsic subtypes: controversies rage on, Curr. Stem Cell Res. Ther., 4:50-60 (2009).

Osipo et al., ErbB-2 inhibition activates Notch-1 and sensitizes breast cancer cells to a gamma-secretase inhibitor, Oncogene, 27:5019-5032 (2008).

Pandya et al., Nuclear localization of KLF4 is associated with an aggressive phenotype in early-stage breast cancer, Clin. Cancer Res., 10:2709-2719 (2004).

Park et al., Cancer stem cell-directed therapies: recent data from the laboratory and clinic, Mol. Ther., 17:219-230 (2009).

Phillips et al., The response of CD24(−/low)/CD44+breast cancer-initiating cells to radiation, J. Natl. Cancer Inst., 98 (24):1777-1785 (2006).

Politi et al., Notch in mammary gland development and breast cancer, Seminars Cancer Biol., 14:341-347 (2004).

Ponti et al., Isolation and in vitro propagation of tumorigenic breast cancer cells with stem/progenitor cell properties, Cancer Res., 65:5506-5511 (2005).

(56) References Cited

OTHER PUBLICATIONS

Raafat et al., Mammary development and tumorigenesis in mice expressing a truncated human Notch4/Int3 intracellular domain (h-Int3sh), Oncogene, 23:9401-9407 (2004).

Reedijk et al., JAG1 expression is associated with a basal phenotype and recurrence in lymph node-negative breast cancer, Breast Cancer Res. Treat, 111:439-448 (2008).

Reedijk et al., High-level coexpression of JAG1 and NOTCH1 is observed in human breast cancer and is associated with poor overall survival, Cancer Res., 65:8530-8537 (2005).

Rizzo et al., Targeting Notch signaling cross-talk with estrogen receptor and ErbB-2 in breast cancer, Adv. Enzyme Regul., 49:134-141 (2009).

Rizzo et al., Cross-talk between notch and the estrogen receptor in breast cancer suggests novel therapeutic approaches, Cancer Res., 68:5226-5235 (2008).

Sansone et al., IL-6 triggers malignant features in mammospheres from human ductal breast carcinoma and normal mammary gland, J. Clin. Invest., 117:3988-4002 (2007).

Shankar, et al., Suberoylanilide hydroxamic acid (Zolinza/vorinostat) sensitizes TRAIL-resistant breast cancer cells orthotopicaly implanted in BALB/c nude mice, Mol. Cancer Ther., 8:1596-1605 (2009).

Stingl et al., Molecular heterogeneity of breast carcinomas and the cancer stem cell hypothesis, Nat. Rev. Cancer, 7:791-9 (2007).

Sun et al., Identification of an antiapoptotic protein complex at death receptors, Cell Death Differ., 15:1887-1900 (2008).

Sussman et al., Chemotherapy-resistant side-population of colon cancer cells has a higher sensitivity to TRAIL than the non-SP, a higher expression of c-Myc and TRAIL-receptor DR4, Cancer Biol. Ther., 6:1490-1495 (2007).

Tanei et al., Association of breast cancer stem cells identified by aldehyde dehydrogenase 1 expression with resistance to sequential paclitaxel and epirubicin-based chemotherapy for breast cancers, Clin. Cancer Res., 15:4234-4241 (2009).

Wang et al., Musashi1 modulates mammary progenitor cell expansion through proliferin-mediated activation of the Wnt and Notch pathways, Mol. Cell Biol., 28:3589-3599 (2008).

Zobalova et al., CD133-positive cells are resistant to TRAIL due to up-regulation of FLIP, Biochem. Biophys. Res. Commun., 373:567-571 (2008).

\* cited by examiner

US 8,703,712 B2

TARGETING CANCER STEM CELLS WITH DR5 AGONISTS

STATEMENT REGARDING FEDERALLY FUNDED RESEARCH

This invention was made with government support under Grant No. CA089019-06-A2 awarded by the National Institutes of Health. The government has certain rights in the invention.

CROSS REFERENCE TO RELATED APPLICATION

This application claims the benefit of U.S. Provisional Application No. 61/315,143, filed on Mar. 18, 2010, which is incorporated by reference herein.

BACKGROUND

Normal tissues and organs contain a population of stem cells capable of self-renewal and recapitulation of the organ or tissue. Cancer stem cells (CSCs) were first detected in patients with acute leukemia and more recently in a variety of solid tumors. These cells have been characterized and isolated for study by phenotype based on cell surface antigens (CD44+ CD24−, CD133, etc.) and by functional activities including enhanced efflux-pumping of a Hoechst dye and over-expression of aldehyde dehydrogenase1 (ALDH1). In general, these tumor CSCs share common characteristics including self-renewal, ability to induce tumors at low cell numbers, ability to produce tumors composed of differentiated and heterogeneous cell profiles, low rates of cell division, gene expression profiles that differ from their more differentiated cell counterparts and resistance to standard chemotherapy and radiation.

SUMMARY

Provided is a method of determining the level of resistance or sensitivity of cancer stem cells to a death receptor agonist. The method includes the steps of acquiring a biological sample from a subject with cancer, wherein the sample contains cancer stem cells and detecting the level of IAP in a DR5/DDX3/IAP complex or a plurality of complexes. A high level of IAP in the complex or complexes indicates resistance of the cancer stem cells to the death receptor agonist. A low level of IAP in the complex or complexes indicates sensitivity of the cancer stem cells to the death receptor agonist. An intermediate level of IAP in the complex or complexes indicates an intermediate level of sensitivity.

Also provided is a method of killing cancer stem cells in a subject. The method includes the steps of determining the level of death receptor agonist resistance or sensitivity of the cancer stem cells and administering to the subject a death receptor agonist if the cells are sensitive or further administering to the subject an IAP inhibitor if the cells are resistant.

Provided is a method of reducing the risk of cancer recurrence in a subject. The method includes the steps of selecting a subject who has been treated for cancer and administering to the subject a death receptor agonist.

The details are set forth in the accompanying drawings and the description below. Other features, objects, and advantages will be apparent from the description and drawings, and from the claims.

DESCRIPTION OF DRAWINGS

In FIG. 6A, the basal cell lines (SUM149, SUM159, SUM102, 2LMP, HCC38, and BT20), which were all very sensitive to anti-DR5 mediated cytotoxicity, had low levels of DR5 associated DDX3 and cIAP1. All the luminal (MDA-MB-134, BT474, MCF7, ZR-75-1, ZR-75-30) and HER2 amplified (MDA-MB-453, DY36T2) cell lines, which were all resistant to anti-DR5 had much higher levels of DR5 associated DDX3 and cIAP1. In FIG. 6B, in the anti-DR5 sensitive cell lines, the molecular weight (MW) of DDX3 co-immunoprecipitated with DR5 was smaller as demonstrated by the anti-C-terminal DDX3 antibody, 3E4.

DETAILED DESCRIPTION

Figure 1:
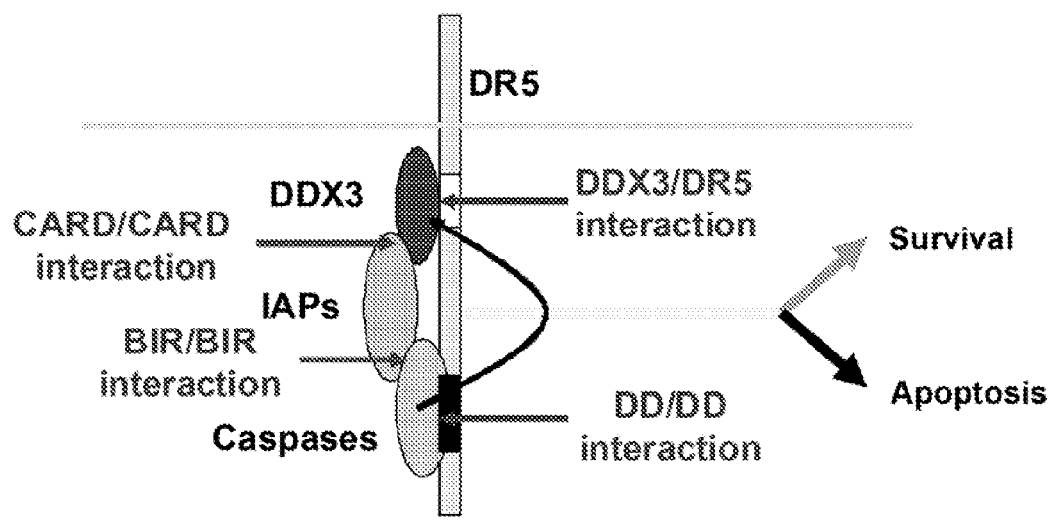
FIG. 1 is a schematic showing the DR5/DDX3/IAPs apoptosis inhibitory complex. This schematic illustrates that the DR5 cytoplasmic tail has at least two functionally distinct domains which interact with each other to determine the apoptosis signal transduction of DR5. When the DDX3/IAP complex is dominant over the death domain complex, cancer cells shift toward resistance to DR5 mediated apoptosis.
Figure 2A:
FIGS. 2A-2D are graphs showing TRA-8 induced cytotoxicity of parental and sorted basal breast cancer cell lines. Aldefluor positive and Aldefluor negative populations of 2LMP (FIG. 2A), SUM159 (FIG. 2B), BT-20 (FIG. 2C), and SUM149 (FIG. 2D) cells were isolated. The parental cells were not subjected to cell sorting. Each population was plated (2,000 cells per well) in non-adherent 96 well black plates and incubated for 24 hours in serum free tumorsphere medium. Cells were then treated with TRA-8 for 24 hours at 37° C., and cell viability was assessed after 24 hours by measuring ATP levels (n=4 replicates). The percentage of Aldefluor+ cells recovered is given for each cell line in parentheses.
Figure 2B:
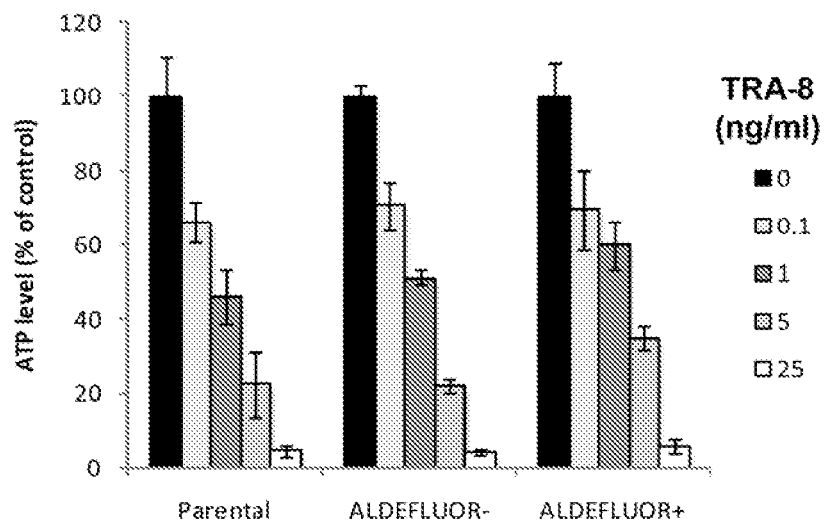
Figure 2C:
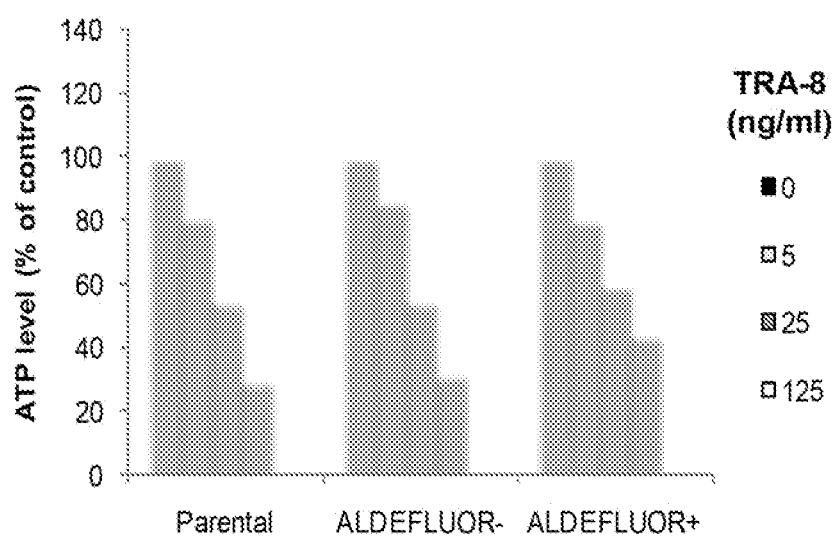
Figure 2D:
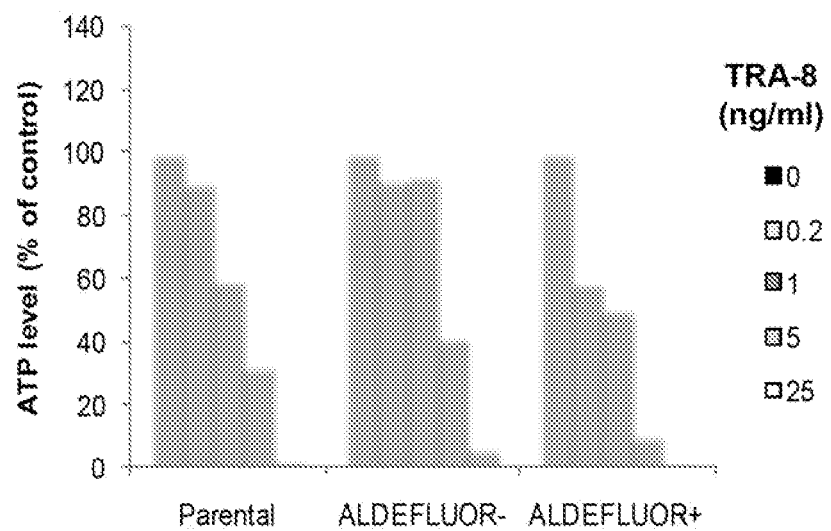

DDX3 (an RNA helicase molecule) is a DR5 associated protein which has a DR5 specific binding site separate from and proximal to the DR5 death domain site. The DDX3 molecule contains a Caspase Recruitment Domain (CARD) at its N-terminus, which is capable of recruiting Inhibitor of Apoptosis proteins (IAPB) through CARD/CARD interaction. The recruited IAPs can inhibit the activity of caspases via their Baculoviral IAP Repeat (BIR) regions, thereby inhibiting initial apoptosis signal transduction at the death domain. FIG. 1 depicts this model, which illustrates that the DR5 cytoplasmic tail has at least two functionally distinct domains that interact with each other to determine the apoptosis signal transduction of DR5. When the DDX3/IAP complex is dominant over the death domain complex, cancer cells shift toward resistance to DR5 mediated apoptosis. As described herein and in the examples below, the DR5/DDX3/IAP complex is associated with the anti-DR5 resistance in several types of human tumor cell lines including breast cancer cell lines.

Provided is a method of determining the level of resistance or sensitivity of cancer stem cells to a death receptor agonist. The method comprises the steps of acquiring a biological sample from a subject with cancer, wherein the sample comprises cancer stem cells and detecting the level of IAP in a DR5/DDX3/IAP complex or complexes in an enriched population of cancer stem cells from the sample. A high level of IAP in one or more complexes of the enriched population of cancer stem cells indicates resistance or lack of sensitivity of the cancer stem cells to a death receptor agonist; whereas a low level of IAP in one or more complexes of the enriched population of cancer stem cells indicates sensitivity or lack of resistance of the cancer stem cells to a death receptor agonist. A medium level of IAP in one or more complexes of the enriched population of cancer stem cells indicates intermediate sensitivity of the cancer stem cells to a death receptor agonist.

High, medium and low levels of IAP, as used herein, refer to a level compared to one or more reference points. For example, a high level of IAP means the level of IAP is approximately the same as or higher than the level of IAP in one or more cells known to be resistant to a death receptor agonist. A low level of IAP means the level of IAP is approximately the same as or lower than the level of IAP in one or more cells known to be sensitive to a death receptor agonist. A medium level of IAP means the level of IAP is approximately the same as or higher than the level of IAP in one or more cells known to have intermediate sensitivity to a death receptor agonist. A medium level of IAP means the level is lower than the level of IAP in one or more cells known to be resistant to a death receptor agonist and higher than the level of IAP in one or more cells known to be sensitive to a death receptor agonist. One of skill in the art will note that a high level of IAP in a complex can be similarly determined by a comparison to a low or medium reference point; a low level as compared to a medium or high reference point and the like. A high or low level is optionally statistically higher or lower than a reference point using at least one acceptable statistical analysis method. It should be noted IAP levels are those present in a complex of DR5/DDX3/IAP. The complex can be "pulled down" or isolated by a variety of methods. For example, it can be pulled down using an antibody to DDX3 or DR5. See, for example, FIG. 6, where the complexes were pulled down with a DR5 antibody and wherein the sensitive cells include those with OD450/655 of IAP of less than 0.25; intermediately sensitive cells have an OD 450/655 of IAP of between 0.25 and 0.5; and sensitive cells have an OD 450/655 of IAP of greater than 0.5. Although such values vary based on assay conditions, they are exemplary.

Assay techniques that can be used to determine levels of IAP proteins in a sample are known. Such assay methods include a radioimmunoassay (RIA), an immunohistochemistry assay, an in situ hybridization assay, a competitive-binding assay, a Western blot analysis, and an ELISA assay. Such assays can be combined with densitometry and optical density or the like for further quantification. Assays also include, but are not limited to, a microarray assay, a gene chip, a Northern blot, an in situ hybridization assay, a reverse-transcription-polymerase chain reaction (RT-PCR) assay, a one step PCR assay, and a real-time quantitative (qRT)-PCR assay. The analytical techniques to determine protein or RNA expression are known. See, e.g., Sambrook et al., Molecular Cloning: A Laboratory Manual, 3$^{rd}$ Ed., Cold Spring Harbor Press, Cold Spring Harbor, N.Y. (2001).

These methods can be used in conjunction with detection methods and/or cell sorting, for example, labeled antibodies (primary, secondary or tertiary) or labeled probes can be used. Fluorescent labels can be detected and used, for example, for sorting.

Techniques to determine levels of a DR5/DDX3/cIAP complex are also known to those of skill in the art. Assays to determine a level of the complex can be selected from the group consisting of an immunoprecipation assay, a co-immunoprecipitation assay, and non-gel based approaches, such as mass spectrometry or protein interaction profiling, such as a co-localization assay. The assays are known in the art. See, e.g., Sambrook et al., Molecular Cloning: A Laboratory Manual, 3rd Ed., Cold Spring Harbor Press, Cold Spring Harbor, N.Y. (2001); Dickson, Methods Mol. Biol. 461:735-44 (2008); and Zinchuk et al., Acta Histochem. Cytochem. 40:101-11 (2007).

Also provided is a method of killing cancer stem cells in a subject. The method comprises determining the level of death receptor agonist resistance or sensitivity of cancer stem cells in a biological sample. If the cancer stem cells are sensitive to the death receptor agonist, the subject is administered a death receptor agonist, and, if the cancer stem cells are resistant to the death receptor agonist, the subject is administered an IAP inhibitor and a death receptor agonist.

In the provided methods, the cancer stem cells are positive for ALDH, CD44, CD133, ESA, or any combination thereof. For example, the cancer stem cells are positive for both ALDH and CD44.

Optionally, the death receptor agonist is a death receptor antibody, TRAIL, or a TRAIL agonist. Optionally, the death receptor antibody is a DR5 or DR4 antibody.

Optionally, the cancer is colon cancer, ovarian cancer, pancreatic cancer, lymphoma, sarcoma, renal cell cancer, prostate cancer, breast cancer, brain cancer (e.g., a glioma or glioblastoma), myeloma, head and neck cancer, lung cancer, liver cancer, melanoma or leukemia. Optionally, the cancer exhibits morphologic and molecular changes characteristic of mesenchymal tissue (i.e., mesenchymal-like cancer) or has a basal-like phenotype (i.e., a basal-like cancer). Optionally, the cancer is metastatic or has a poor prognosis or is invasive. Optionally, the cancer is breast cancer, for example, triple negative breast cancer. By triple negative breast cancer is meant estrogen-receptor (ER) negative, progesterone-receptor (PR) negative, and HER2 negative breast cancer. Stated differently, triple negative breast cancers do not express ER, PR, or HER2.

As used herein a biological sample which is subjected to testing is a sample derived from a subject and includes, but is not limited to, any cell, tissue or biological fluid. The sample can be, but is not limited to, peripheral blood, plasma, urine, saliva, gastric secretion, bone marrow specimens, a tumor biopsy or tumor tissue from a tumor resection. The biological sample can also be whole cells, cell organelles (e.g., nuclei) or cell compartments (e.g., membrane). A biological sample can also include a partially purified sample, cell culture, or a cell line derived from a subject.

By death receptor is meant a receptor that induces cellular apoptosis upon activation. Death receptors include, for example, tumor necrosis factor (TNF) receptor superfamily members having death domains (e.g., TNER1, Fas, DR4, and DR5).

Signal transduction through, for example, DR5 is a key mechanism in the control of DR5-mediated apoptosis. A common feature of the death receptors of the TNFR superfamily is that they all have a conserved death domain in their cytoplasm tail (Zhou et al., Immunol. Res. 26:323-36 (2002)). DR5-mediated apoptosis is initiated at the death domain. Crosslinking of DR5 at the cell surface by TRAIL or agonistic anti-DR5 antibody leads to oligomerization of DR5, which is followed by the recruitment of FADD to the death domain of DR5 (Bodmer et al., Nat. Cell Biol. 2:241-3 (2000); Chaudhary et al., Immunity 7:821-30 (1997); Kuang et al., J. Biol. Chem. 275:25065-8 (2000); Schneider et al., Immunity 7:831-6 (1997); Sprick et al., Immunity 12:599-609 (2000)). The death-domain engaged FADD further recruits the initiator procaspase 8 and/or procaspase 10 to form a death inducing signaling complex (DISC) through homophilic death domain (DD) interactions (Krammer, Nature 407:789-95 (2000)). Activated caspase 8 and 10 may activate caspase 3 directly or may cleave BID, a pro-apoptotic Bcl2 protein containing the Bcl-2 homology (BH) domain 3, to activate a mitochondria-dependent apoptosis pathway through release of cytochrome C and caspase 9 activation (Desagher and Martinou, Trends Cell Biol. 10:369-77 (2000); Scaffidi et al., EMBO J. 17:1675-87 (1998)). Following the formation of the death domain complex, several signal transduction pathways are activated such as caspase, NF-κB, and JNK/p38. Activation of these signaling pathways leads to regulation of death receptor-mediated apoptosis through the Bcl-2 and IAP family of proteins.

By agonist is meant a substance (molecule, drug, protein, etc.) that is capable of combining with a receptor death receptor) on a cell and initiating the same reaction or activity typically produced by the binding of the endogenous ligand (e.g., apoptosis). The agonist of the present method can be a death receptor ligand. Thus, the agonist can be TNF, Fas Ligand, or TRAIL. The agonist can further be a fragment of these ligands comprising the death receptor binding domain such that the fragment is capable of binding and activating the death receptor. The agonist can further be a fusion protein comprising the death receptor binding domain such that the fusion protein is capable of binding and activating the death receptor. The agonist can further be a polypeptide having an amino acid sequence with at least 85%, 90%, 95%, or 99% homology to TNF, Fas, TRAIL or their death receptor binding domain regions, such that the homologue is capable of binding and activating the death receptor.

The agonist can further be an apoptosis-inducing antibody that binds the death receptor. The antibody can be monoclonal, polyclonal, chimeric, single chain, humanized, fully human antibody, or any Fab or F(ab')2 fragments thereof. By apoptosis-inducing antibody is meant an antibody that causes programmed cell death either before or after activation using the methods provided herein. Thus, the agonist of the present method can be an antibody specific for a Fas, TNFR1 or TRAIL death receptor, such that the antibody activates the death receptor. The agonist can be an antibody specific for DR4 or DR5. The agonist can be a DR5 antibody having the same epitope specificity as an antibody produced by, or secreted by, a mouse-mouse hybridoma having ATCC Accession Number PTA-1428 (e.g., the TRA-8 antibody), ATCC Accession Number PTA-1741 (e.g., the TRA-1 antibody), ATCC Accession Number PTA-1742 (e.g., the TRA-10 antibody). The agonist can be a DR4 antibody having the same epitope specificity as an antibody produced by, or secreted by, the hybridoma having ATCC Accession Number PTA-3798 (e.g., the 2E12 antibody). Optionally, the agonist is a humanized version of the antibody produced by mouse-mouse hybridoma having ATCC Accession Number PTA-1428 or a humanized version of the antibody produced by mouse-mouse hybridoma having ATCC Accession Number PTA-3798.

The TRAIL receptor targeted by the antibody of the present method can be DR4 or DR5. Such receptors are described in published patent applications WO99/03992, WO98/35986, WO98/41629, WO98/32856, WO00/66156, WO98/46642, WO98/5173, WO99/02653, WO99/09165, WO99/11791, WO99/12963 and published U.S. Pat. No. 6,313,269, which are all incorporated herein by reference in their entireties for the receptors taught therein. Monoclonal antibodies specific for these receptors can be generated using methods known in the art. See, e.g., Kohler and Milstein, Nature, 256:495-7 (1975) and Eur. J. Immunol. 6:511-9 (1976), both of which are hereby incorporated by reference in their entirety for these methods. See also methods taught in published patent application WO01/83560, which is incorporated herein by reference in its entirety.

Provided is a method of reducing the risk of cancer recurrence in a subject. The method comprises selecting a subject who has been treated for cancer and administering to the subject a death receptor agonist. Optionally, the death receptor agonist is a death receptor antibody, for example, a DR5 or DR4 antibody.

Optionally, the method further comprises administering to the subject one or more agents selected from the group consisting of an IAP inhibitor, a NOTCH inhibitor, and a chemotherapeutic agent.

Inhibitor of Apoptosis Protein (IAP) family proteins, referred to generically herein as IAP, are overexpressed in many cancer cell types. The IAP family antagonizes cell death by interacting with and inhibiting the enzymatic activity of mature caspases. Eight distinct mammalian IAPs have been identified, including XIAP, c-IAP1, c-IAP2, and ML-IAP/Livin (see, for example, Ashhab et al., FEBS Lett. 495: 56-60 (2001); Kasof and Gomes, J. Biol. Chem. 276:3238-46 (2001); Vucic et al., Curr. Biol. 10:1359-66 (2000)). All IAPs contain one to three baculovirus IAP repeat (BIR) domains and have homologous sequence. Through the BIR domain, IAP molecules bind and directly inhibit caspases (Deveraux and Reed, Genes Dev. 13:239-52 (1999); Deveraux et al., Nature 388:300-4 (1997)). The mitochondrial proteins Smac/DIABLO could bind to and antagonize IAPB (Suzuki et al., J. Biol. Chem. 276:27058-63 (2001)) to suppress IAP function (Wieland et al., Oncol. Res. 12:491-500 (2000)). Optionally, the IAP inhibitor is AT-406, HGS1029, Embelin (Mori et al., J. Surg. Res. 142:281-6 (2007)), XIAP inhibitor 1 or XIAP inhibitor 2 (Fakler et al., Blood, 113:1710-22 (2009)). Optionally, the IAP inhibitor is an antisense molecule, for example, an siRNA.

Over-expression of NOTCH and/or its ligands has been associated with poor prognosis cancers. Treatment of ER/PR positive breast cancer with anti-estrogens or treatment of HER2 positive breast cancer with Herceptin activates their NOTCH pathways and sensitizes these cells to anti-NOTCH therapy (gamma secretase inhibitors). Triple negative (basal-like genotype) breast cancer cells have baseline activation of NOTCH 1 and 4 and NOTCH inhibition inhibits their proliferation and has anti-tumor efficacy in murine xenograft models. Thus, optionally, the Notch inhibitor is a gamma secretase inhibitor, an antibody (Aste-Amezaga et al., PLoS One 5:e9094 (2010)), a small molecule inhibitor, e.g., MRK003, (Shelton et al., PNAS 106:20228-33 (2009)), microRNA (Song et al., JBC 284:31921-7 (2009)), or natural products (Sarkar et al., Cell Signal. 21:1541-7 (2009)).

Optionally, the chemotherapeutic agent is selected from the group consisting of adriamycin, bleomycin, carboplatin, chlorambucil, cisplatin, colchicines, cyclophosphamide, daunorubicin, dactinomycin, diethylstilbestrol, etoposide, 5-fluorouracil, floxuridine, melphalan, methotrexate, mitomycin, 6-mercaptopurine, paclitaxel, teniposide, 6-thioguanine, vincristine, and vinblastine. Further examples of chemotherapeutic agents are found in The Merck Manual of Diagnosis and Therapy, 18$^{th}$ Ed., Berkow et al., eds, Rahway, N.H. (2005) and Sladek et al., Metabolism and Action of Anti-Cancer Drugs, Powis et al., eds., Taylor and Francis, New York, N.Y. (1987).

In the method of reducing the risk of recurrence of cancer in a subject, the subject has been treated for cancer. Optionally, the cancer treatment comprises surgical removal of a tumor, radiation, or treatment with one or more chemotherapeutic agents. Optionally, the administration step occurs after surgical removal of a tumor, radiation, or treatment with one or more chemotherapeutic agents. Optionally, the subject is clinically disease free.

The risk of any cancer can be reduced using the provided method, for example, whether the cancer is a primary cancer or a metastatic cancer. Optionally, the cancer is triple negative breast cancer or any cancer mentioned herein.

Optionally, the subject is tested prior to treatment to determine whether the cancer cells and/or cancer stem cells are resistant or sensitive to a death receptor agonist. The cancer cells or cancer stem cells of the subject were, for example, resistant to a death receptor agonist (e.g., DR5 antibody). Furthermore, the cancer or cancer stem cells of the subject, prior to treatment, can be assessed for the presence of a DDX3 mutant (e.g., lacking a functional N-terminal CARD domain).

Optionally, the method further includes the step of isolating cancer stem cells from the subject. This step can occur, for example, prior to the cancer treatment or subsequent to cancer treatment if the cancer stem cells are detectable. Optionally, the cancer stem cells are positive for ALDH, CD44, CD 133, ESA or a combination thereof. Optionally, the cancer stem cells are positive for both ALDH and CD44. Optionally, the method further includes the step of detecting the level of IAP in a DR5/DDX3/IAP complex in an enriched population of cancer stem cells from the subject. Optionally, the method further includes detecting cancer stem cells with a mutant DDX3, wherein the DDX3 lacks a functional CARD domain.

As used herein, a subject that is clinically disease free refers to a condition when a subject has received definitive therapy (e.g., surgery, radiation, chemotherapy or any combination thereof) and has no clinically detectable residual cancer based on at least one or more of a physical exam, an x-ray, a CT scan, an MRI, a PET scan, or tissue analysis (e.g., biopsy, bone marrow analysis, blood analysis).

Provided herein are methods of killing cancer stem cells and methods of reducing cancer recurrence in a subject. Such methods include administering an effective amount of a death receptor agonist. The death receptor agonist can be administered with an IAP inhibitor, a Notch inhibitor, a chemotherapeutic agent, radiation, or combinations thereof. Optionally, the death receptor agonist, IAP inhibitor, Notch inhibitor, chemotherapeutic agent, and combinations thereof are contained within one or more pharmaceutical compositions. The administration of the death receptor agonist with one or more other agents can be sequential or concomitant. Concomitant administration, optionally, occurs using separate compositions each containing one administrated agent.

Provided herein are compositions containing the provided death receptor agonist with an IAP inhibitor, a Notch inhibitor, a chemotherapeutic agent, or any combinations thereof, and a pharmaceutically acceptable carrier described herein. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in Remington: The Science and Practice of Pharmacy, 21st Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the death receptor agonist, IAP inhibitor, Notch inhibitors, chemotherapeutic agent, and combinations thereof to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation; or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, antioxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Administration of compounds described herein or pharmaceutically acceptable salts or prodrugs thereof can be carried out using therapeutically effective amounts of the compounds described herein or pharmaceutically acceptable salts or prodrugs thereof for periods of time effective to kill cancer stem cells or reduce cancer recurrence. The effective amount of the compounds described herein or pharmaceutically acceptable salts or prodrugs thereof can be determined by one of ordinary skill in the art and can be administered in a single dose or in the form of individual divided doses, such as from 1 to 4 times per day. Those of skill in the art will understand that the specific dose level and frequency of dosage for any particular subject will vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a composition or therapeutic agent, that occurs before or at about the same time a subject begins to show one or more symptoms of the disease or disorder, which inhibits or delays onset or severity of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

The examples below are intended to further illustrate certain aspects of the methods and compounds described herein, and are not intended to limit the scope of the claims.

EXAMPLES

Materials and Methods

Drugs and Antibodies. Adriamycin and Taxol were purchased from Sigma Aldrich Chemical Co. (St. Louis, Mo.) and prepared as 10 mM stock solutions in distilled $H_2O$ or DMSO, respectively. Purified TRA-8 (IgG1) mAb was prepared as described previously (Ichikawa et al., Nat. Med. 7:954-60 (2001) and WO01/83560). Isotype-specific IgG1 control antibody was obtained from Southern Biotechnology Associates (Birmingham, Ala.). Anti-DR4 mAb 2E12 (IgG1, k) was described previously (WO03/37913). Super Killer TRAIL™ was purchased from Alexis Biochemicals (Plymouth Meeting, Pa.). Conjugated antibodies APC mouse anti-human CD44, PE-Cy7 rat anti-mouse CD44, and corresponding isotype control antibodies were purchased from BD Pharmingen (San Jose, Calif.). ALDEFLUOR® kit including diethylaminobenzaldehyde (DEAB) negative control was obtained from StemCell Technologies (Durham, N.C.). Cleaved caspase-8 rabbit mAb and cleaved caspase-3 rabbit mAb were purchased from Cell Signaling (Billerica, Mass.). Secondary antibodies, Alexa fluor 405 goat anti-rabbit IgG and Alexa fluor 647 goat anti-mouse IgG1 were purchased from Invitrogen (Carlsbad, Calif.).

Cells and Cell Culture. The 2LMP subclone of the human breast cancer cell line MDA-MB-231 was maintained in improved MEM supplemented with 10% FBS (Hyclone; Logan, Utah). Basal-like cell lines HCC38, HCC1187, HCC1143, MDA-MB-436, BT-20, BT-549 were obtained from American Type Culture Collection (Manassas, Va.) and cultured according to supplier's directions with the exception of MDA-MB-436, which was grown in DMEM supplemented with 10 μg/mL insulin, glutathione, and 10% FBS. SUM159 was obtained from Asterand (Detroit, Mich.) and grown according to supplier's recommendation. All cell lines were maintained in antibiotic-free medium at 37° C. in a 5% $CO_2$ atmosphere and routinely screened for Mycoplasma contamination. Sorted cells and tumorspheres were maintained in MEGM medium (Lonza, Walkersville, Md.).

Breast Cancer Stem Cells (BCSC) Isolation by Flow Cytometry. Basal-like cell lines were plated in T75 flasks (Costar; Cambridge, Mass.) in corresponding media and harvested at 75% confluence. BCSC markers were analyzed on attached bulk cell populations. Cells were harvested with trypsin and labeled with 1 μL of ALDEFLUOR® reagent in 100 μL ALDEFLUOR® buffer per $5 \times 10^6$ cells and incubated at 37° C. for 30 minutes. Cells were then labeled with APC-CD44 (1:25) and PE-CD24 (1:25) in 200 μL of ALDEFLUOR® buffer on ice for 15 minutes. The ALDEFLUOR® positive population was established by using $2 \times 10^6$ ALDEFLUOR® labeled cells and 5 μL DEAB in 200 μL ALDEFLUOR® buffer. Samples were sorted on a Becton-Dickinson-FACSAriaII™ or analyzed on Becton-Dickinson-LSRII™ flow cytometer (Chicago, Ill.). Data were evaluated using FlowJo software (FlowJo; Ashland, Oreg.).

DR5 Expression and Functional Caspase Activation. 2LMP, SUM159 and HCC1143 cell lines were harvested using cell stripper (Mediatech; Manassas, Va.) to prevent cleavage of death receptor. Cells were incubated with ALDEFLUOR reagents for 30 minutes at 37° C. Cells were then labeled on ice with TRA-8 (IgG1) or IgG1 isotype control for 15 minutes. Cells were then incubated with CD44-PE-Cy7 (1:1000), CD24-PE (1:100) and secondary antibody (Alexa-647) (1:100) for 15 minutes on ice. Samples were analyzed by flow cytometry for DR5 expression on the $ALDH^+/CD44^+/CD24^-$ subpopulation. Analysis of caspase 8 and 3 activation of BCSC after treatment was accomplished by harvesting cells using cell stripper and treating ~$1 \times 10^7$ cells with 1 μg/mL TRA-8 for 2 hours in MEGM medium+2% BSA. Cells were sorted for the ALDH+ population, and then fixed with 1% paraformaldehyde for 5 minutes on ice. Fixed cells were labeled with CD44-APC and CD24-PE (1:100) on ice for 15 minutes. Cells were then permeabilized using 3% BSA, 0.1% saponin in 200 μL PBS on ice for 15 minutes and labeled with cleaved caspase 3 or 8 (1:500) on ice for 15 minutes. Cells were incubated with secondary antibody Alexa-405 anti-rabbit (1:100) on ice for 15 minutes. Samples were kept in 0.1% saponin and analyzed by flow cytometry.

Cell Viability Assays Using ATPLite. Sorted $CD44^+/CD24^-/ALDH^+$ cells were plated on ultra-low attachment plates (Costar®; Corning Life Sciences; Lowell, Mass.) at 2,000 cells per 50 μL of MEGM medium. Bulk unseparated cells were collected from total viable gates established by forward and side scatter parameters (this controls for any variables introduced by sorting the cells). Cells from the bulk unseparated populations were plated in optically clear 96-well black plates (Costar®) in corresponding media. Sorted and bulk cells were treated with (0.1, 1, 10, 100 or 1000 ng/mL) of TRA-8 immediately after plating and incubated for 24 hours at 37° C. TRA-8 was diluted in culture medium immediately before use. Cell viability was determined by measurement of cellular ATP levels using the ATPLite luminescence-based assay (Packard Instruments, Meriden, Conn.). The manufacturer's recommended protocol was followed with the exception that all reaction volumes (culture medium and reagents) were reduced by one-half. All samples were assayed in quadruplicate and are reported as the mean±SD from a minimum of three independent experiments.

In Vitro Treatment of Tumorspheres. 2LMP and SUM159 cell lines were sorted for ALDH+ cells. Approximately ~$1 \times 10^6$ cells were allowed to form primary spheres at a density of 100,000 cells/mL for 3-4 days in MEGM medium. Tumorspheres were mechanically dissociated and plated in ultra-low attachment 96-well plates (Costar®) at 2,000 cells per well. TRA-8 anti-DR5, 2E12 anti-DR4, TRAIL, IgG isotype control, Adriamycin and Taxol were immediately added to dissociated cells and incubated at 37° C. for 48 hours. Tumorspheres were visually counted using a reticle eye piece. Mean tumorsphere inhibition was calculated relative to untreated control spheres and assays were run in quadruplicate. Three independent experiments were conducted per cell line.

Ex Vivo Treatment of BrCSC and Tumor Implantation. ALDH+/CD44+/CD24− 2LMP and SUM159 cells (1×10⁶) were sorted and allowed to recover for 13 hours in MEGM medium in ultra-low attachment plates at 37° C. After 13 hours cells were separated into treatment groups and drug or antibody was added (lizG, 20 nM, ~3 µg/mL), 2E12 (20 nM), TRA-8 (20 nM), and Adriamycin (500 nM). Cells were treated for 3 hours at 37° C. and then 200 µL (1:1 Matrigel™; BD Biosciences; Franklin Lakes, N.J.) was injected into the mammary fat pad of 4 week old NOD/SCID mice (Harlan, Prattville, Ala.). Tumor size was determined by the product of two largest diameters. Two duplicate experiments were conducted.

Statistical Analysis. A nonlinear model [y=Min+(Max−Min)/(1+dose/β)α; (Rodbard, Clin. Chem. 20:1255-70 (1974); DeLean et al., Am. J. Physiol. 235:E97-102 (1978)), was applied to calculate TRA-8$IC_{50}$, wherein y is the response, the variable β represents $IC_{50}$, the variable α is used to scale concentration for proper transformation, and Min and Max represent the minimum and the maximum of response, respectively. A SAS procedure NLIN was used for the computation (SAS Institute, Inc.; Cary, N.C.). Secondary tumorsphere inhibition was quantified as a mean of tumorsphere inhibition and calculated relative to untreated control, and the data represent the mean of the samples run in quadruplicate.

Example 1

Sensitivity of Breast Cancer Cell Lines to Anti-DR5 (TRA-8) Mediated Cytotoxicity A panel of 26 breast cancer cell lines were examined for sensitivity ($IC_{50}$) to TRA-8 mediated cytotoxicity (Table 1 and 2). Eleven of 15 basal-like cell lines were highly sensitive ($IC_{50}$<100 ng/ml) to anti-DR5 mediated cytotoxicity including all basal B subtype. In contrast, all luminal and HER2 cell lines were resistant.

TABLE 1

TRA-8 cytotoxicity with luminal, HER2 luminal and HER2 basal breast cancer cell lines.

| Phenotype | Cell line | $IC_{50}$ TRA-8 (ng/ml) |
|---|---|---|
| Luminal A (HER2−/ER+) | MCF-7 | >1,000 |
| | T-47D | >1,000 |
| Luminal B (HER2+/ER+) | ZR-75-1 | >1,000 |
| | MDA-MB-134 | >1,000 |
| HER2 amplified luminal (ER+) | BT-474 | >1,000 |
| | DY36T2 | >1,000 |
| | ZR-75-30 | >1,000 |
| HER2 amplified luminal (ER−) | MDA-MB-453 | >1,000 |
| | SK-BR-3 | >1,000 |
| Basal (HER2+ amplified/ER−) | HCC1569 | >1,000 |
| | HCC1954 | >1,000 |

TABLE 2

TRA-8 cytotoxicity with basal breast cancer cell lines.

| Phenotype | Cell line | $IC_{50}$ TRA-8 (ng/ml) |
|---|---|---|
| TNBC (Basal A) | SUM102 | 7.8 |
| | MDA-MB-468 | 30 |
| | HCC1187 | 69 |
| | BT-20 | 92 |
| | HCC1937 | 666 |
| | HCC70 | >1,000 |
| | HCC1143 | >1,000 |
| | HCC1599 | >1,000 |

TABLE 2-continued

TRA-8 cytotoxicity with basal breast cancer cell lines.

| Phenotype | Cell line | $IC_{50}$ TRA-8 (ng/ml) |
|---|---|---|
| TNBC (Basal B) | SUM149 | 0.7 |
| | HCC38 | 1.2 |
| | 2LMP | 1.5 |
| | SUM159 | 3.0 |
| | MDA-MB-436 | 7.2 |
| | MDA-MB-157 | 22 |
| | BT-549 | 65 |

Example 2

Anti-DR5 Sensitive Breast Cancer Cell Lines have ALDH Positive Subpopulations (Breast CSC Enriched)

Breast cancer cell line sensitivity to anti-DR5 cytotoxicity involved the same cell lines reported to have a high frequency of ALDH1 cell populations enriched for CSCs and that this could allow study of such CSC enriched cell populations. Table 3 provides our analysis of 8 anti-DR5 sensitive cell lines in regards to ALDH positive cell content and compares our findings with those reported by the Wicha group (Charafe-Jauffret et al., Cancer Research 69:1302-13 (2009)).

TABLE 3

Aldefluor populations in anti-DR5 sensitive breast cancer cell lines

| Cell line | UAB % Aldefluor+ | Wicha % Aldefluor+ |
|---|---|---|
| BT-20 | 10 | 0.4 ± 0.2 |
| SUM149 | 5-14 | 6 ± 2.2 |
| HCC38 | 38-87 | 98.2 ± 3.4 |
| 2LMP | 1-7 | 0.9 ± 0.7* |
| SUM159 | 1-15 | 5.5 ± 3.4 |
| MDA-MB-436 | 25 | 2.6 ± 1.1 |
| MDA-MB-157 | 0.2-1.2 | 1.2 ± 0.3 |
| BT549 | 9 | ND |

*Results reported for the parental cell line MDA-MB-231

It has been reported that the ALDH positive CSC population contains a subpopulation of CD44+/CD24− cells (ALDH1+/CD44+/CD24−) which can induce breast tumors in immunosuppressed mice with as few as 20 cells. In basal breast cancer cell lines the presence of this ALDH+/CD44+/CD24− population was confirmed as depicted in Table 4.

TABLE 4

Presence of ALDH+/CD44+/CD24− population in breast cancer cell lines

| Phenotype | Cell line | % Aldefluor+ | % ALDH+/CD44+/CD24− |
|---|---|---|---|
| TNBC (Basal B) | 2LMP (n = 2) | 12 | 5 |
| | SUM159 (n = 4) | 8 | 3 |
| | HCC38 (n = 2) | 56 | 16 |
| | SUM149 (n = 4) | 21 | 7 |
| | BT-549 (n = 1) | 7 | 3 |
| | MB-436 (n = 1) | 17 | 2 |
| TNBC (Basal A) | HCC1143 (n = 1) | 15 | 7 |
| | HCC70 (n = 1) | 50 | 8 |
| | HCC1187 (n = 1) | 34 | 2 |
| Luminal A | T-47D (n = 3) | 36 | 0 |

Example 3

Anti-DR5 Mediated Cytotoxicity of ALDH Positive Subpopulation of Breast Cancer Cell Lines The membrane expression of DR5 on ALDH positive and negative cell populations (SUM159, SUM149, 2LMP) was examined and it was found that DR5 expression was comparable on the two populations. Thus, the CSC enriched ALDH populations express membrane DR5.

The ALDH positive and negative cell populations were isolated from four breast cancer cell lines, which were highly sensitive to anti-DR5 mediated cytotoxicity. As illustrated in FIG. 2, the ALDH positive subpopulations varied from 5-10% of the original cell line population and exhibited comparable sensitivity to anti-DR5 mediated cytotoxicity as the ALDH negative cell population. Thus, these 4 cell line CSC enriched ALDH positive populations are very sensitive to anti-DR5 mediated cytotoxicity (doses <100 ng/ml).

Figure 3A:
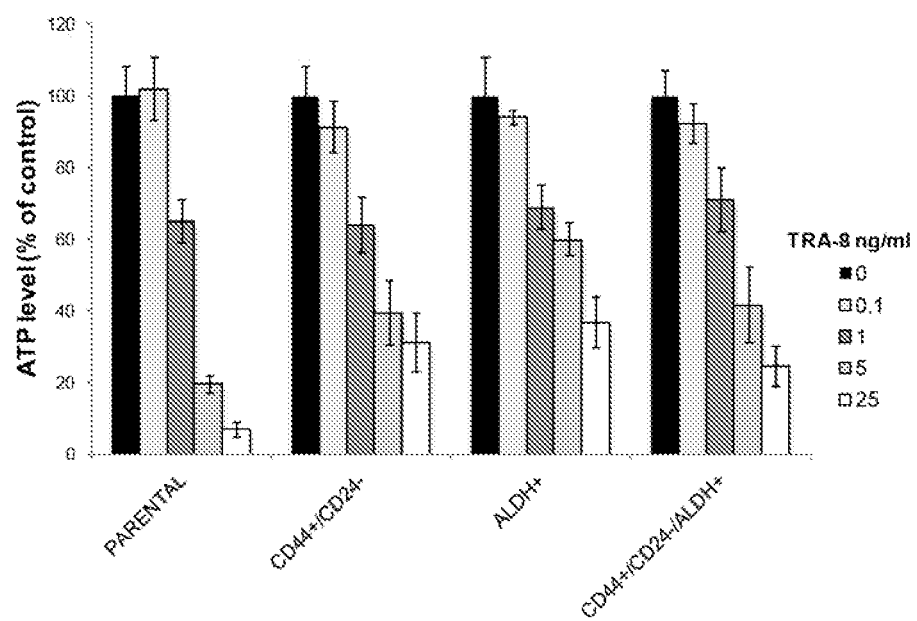
FIGS. 3A and 3B are graphs showing TRA-8 induced cytotoxicity of parental and sorted basal breast cancer cell lines. CD44+/CD24−, ALDH positive, and CD44+/CD24−/ALDH+ populations of 2LMP (FIG. 3A) and SUM159 (FIG. 3B) cells were isolated. The parental cells were not subjected to cell sorting. Each population was plated (2,000 cells per well) in non-adherent 96 well black plates and incubated for 24 hours in serum free tumorsphere medium. Cells were then treated with TRA-8 for 24 hours at 37° C., and cell viability was assessed after 24 hours by measuring ATP levels (n=4 replicates).
Figure 3B:
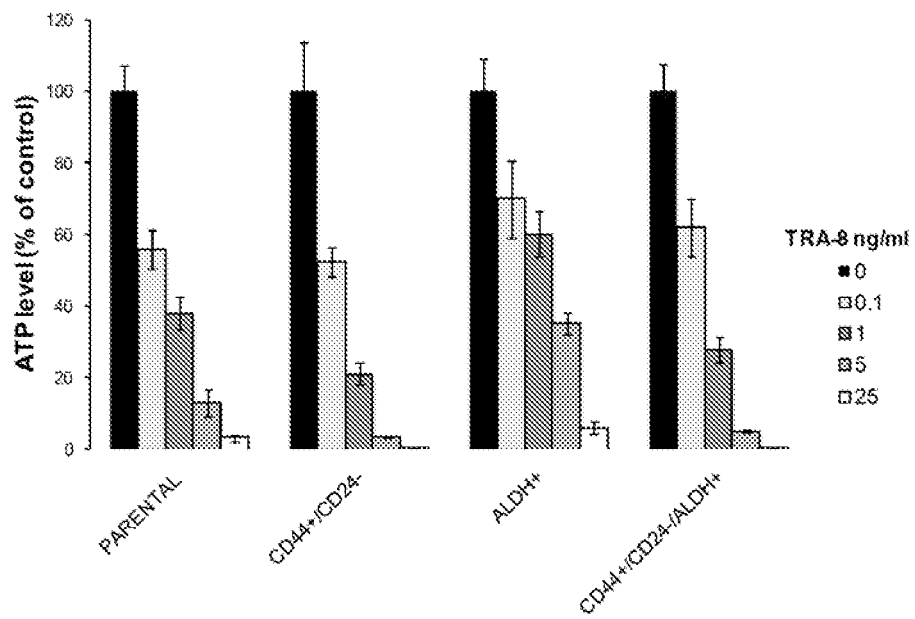

To further pursue this issue, the $CD44^+/CD24^-$ stem cell enriched populations and the doubly enriched $CD44^+/CD24^-$ component of the ALDH positive fraction of tumor cells ($ALDH^+/CD44^+/CD24^-$) were examined. As seen in FIG. 3, the $CD44^+/CD24^-$ population and the doubly enriched $ALDH^+/CD44^+/CD24^-$ retained anti-DR5 mediated cytotoxicity at low doses of TRA-8.

Figure 4A:
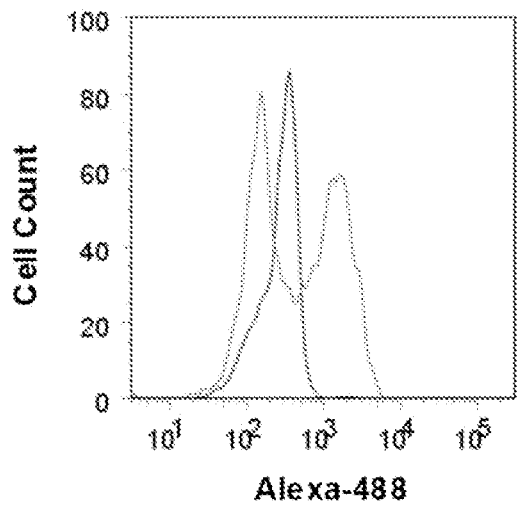
FIGS. 4A and 4B are graphs showing flow cytometry analysis of the ALDH+/CD44+/CD24− population and caspase activation in 2LMP cells. ALDH positive cells were sorted then incubated with 100 ng/ml TRA-8 or control medium for 3 hours. Cells were washed, fixed, and stained with APC-conjugated CD44 and PE-conjugated CD24 antibodies or fluorescent isotype control antibodies. Cells were then washed, permeabilized and stained with antibodies to activated caspases followed by ALEXA 488-conjugated secondary antibody. CD44 and CD24 positive cell populations were identified based on gates established using isotype control antibodies. Caspase 8 (FIG. 4A) and caspase 3 (FIG. 4B) activation in TRA-8 treated (line with two peaks) or untreated (line with one peak) 2LMP cells gated for ALDH+/CD44+/CD24− expression.
Figure 4B:
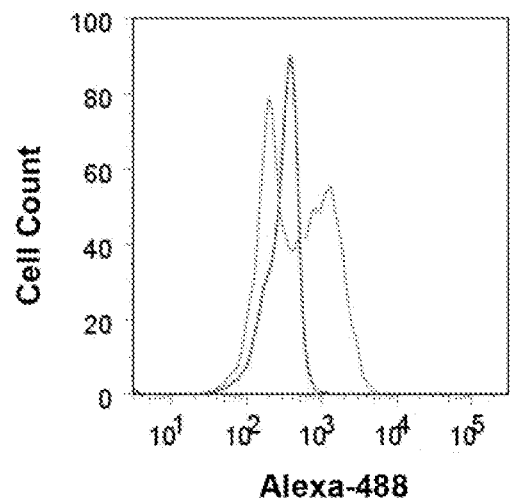

To demonstrate triggering of apoptosis in these CSC doubly enriched cell populations, the ALDH positive fraction of the 2LMP breast cancer cell line was isolated and exposed to aliquots of TRA-8 (100 ng/ml) or control media for 3 hours at 37° C. The two aliquots were then stained for CD44, CD24, and activated caspase 8 or caspase 3. FIG. 4A illustrates the fluorescent analysis for activated caspase 8 in the $CD44^+/CD24^-$ cell quadrant while FIG. 4B provides the same analysis for activated caspase 3. As can be seen, a substantial portion of the $ALDH^+/CD44^+/CD24^-$ population had activated caspase 8 (40%) and 3 (36%) at 3 hour exposure to anti-DR5 (line with two peaks) as compared to control media (line with one peak). Almost identical results were seen with the same analysis of SUM159 $ALDH^+/CD44^+/CD24^-$ breast tumor cells.

Example 4

Anti-DR5 Effect on ALDH Positive Cell Subpopulation Tumorigenicity

Figure 5:
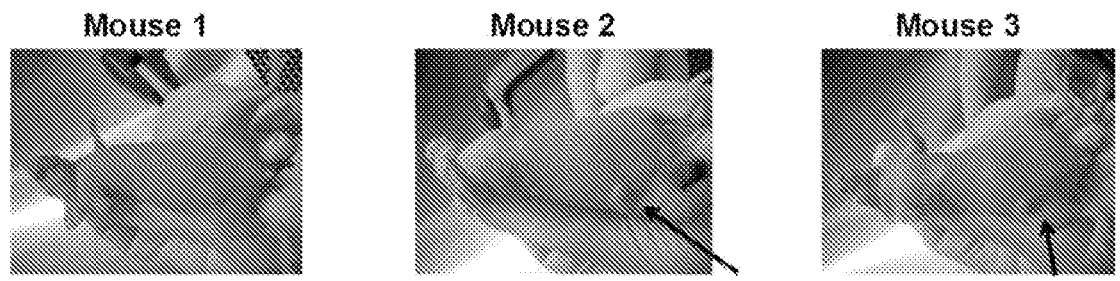
FIG. 5 are photographs showing tumorigenicity of ALDH+ SUM159 cells with or without TRA-8 treatment. Photographs were taken at day 40 after implantation.
Figure 5:
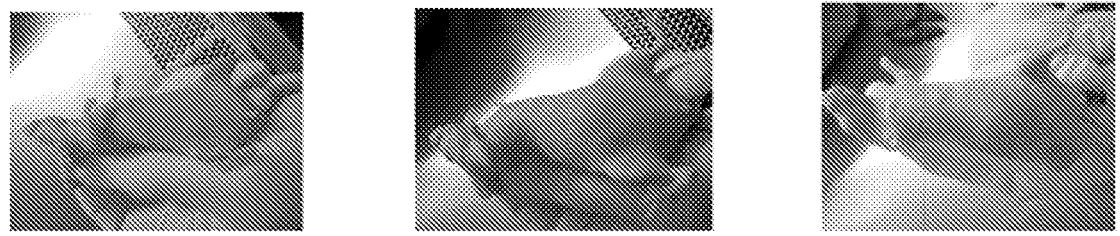

An experiment to assess the effect of low doses of anti-DR5 on the tumorigenicity of the $ALDH^+$ cell population was carried out. SUM159 cells were sorted by flow cytometry using the ALDH assay. $ALDH^+$ cells were not treated or treated with 25 ng/ml TRA-8 for 3 hours, then $1\times10^5$ cells were mixed 50:50 with Matrigel and injected into the mammary fat pad of recipient athymic nude mice. As shown in FIG. 5, 2 of 3 mice implanted with untreated SUM159 ALDE-FLUOR®+ cells showed tumor growth at 40 days post-transplant, whereas 0 of 3 mice implanted with TRA-8 treated $ALDH^+$ cells had developed tumors within 40 days. This study shows inhibition of the tumorigenicity of breast CSC enriched cell population by anti-DR5.

Example 5

Figure 6A:
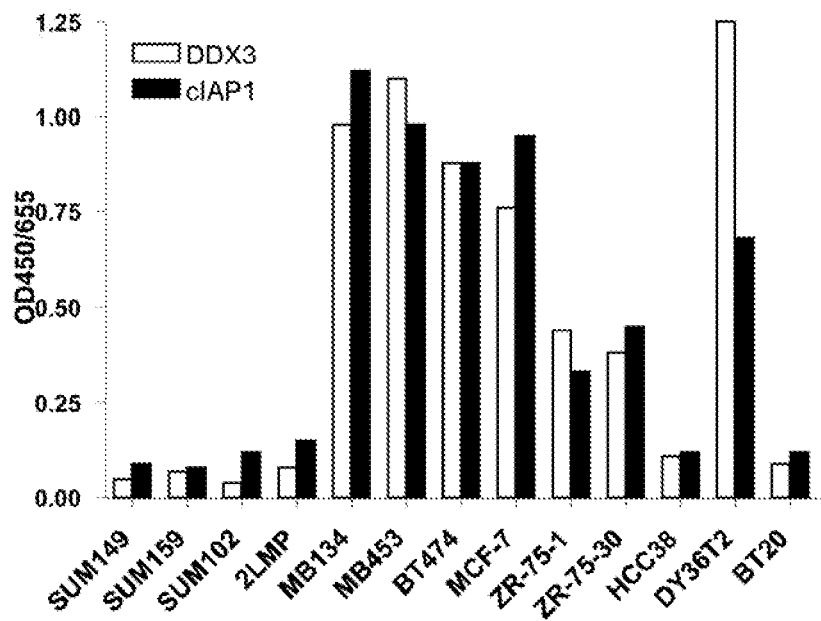
FIG. 6A is a graph and FIG. 6B is a Western blot image showing the DR5/DDX3/cIAP1 protein complex in breast cancer cell lines.

Breast Cancer Cell Line Sensitivity to Anti-DR5 Cytotoxicity and DR5/DDX3/cIAP Complex The DR5/DDX3/cIAP complex was examined in a panel of 13 breast cancer cell lines of known anti-DR5 sensitivity. As illustrated in FIG. 6A, the basal cell lines (SUM149, SUM159, SUM102, 2LMP, HCC38, and BT20), which were all very sensitive to anti-DR5 mediated cytotoxicity had low levels of DR5 associated DDX3 and cIAP1. All the luminal (MDA-MB-134, BT474, MCF7, ZR-75-1, ZR-75-30) and HER2 amplified (MDA-MB-453, DY36T2) cell lines that were all resistant to anti-DR5 had much higher levels of DR5 associated DDX3 and cIAP1.

Figure 6B:
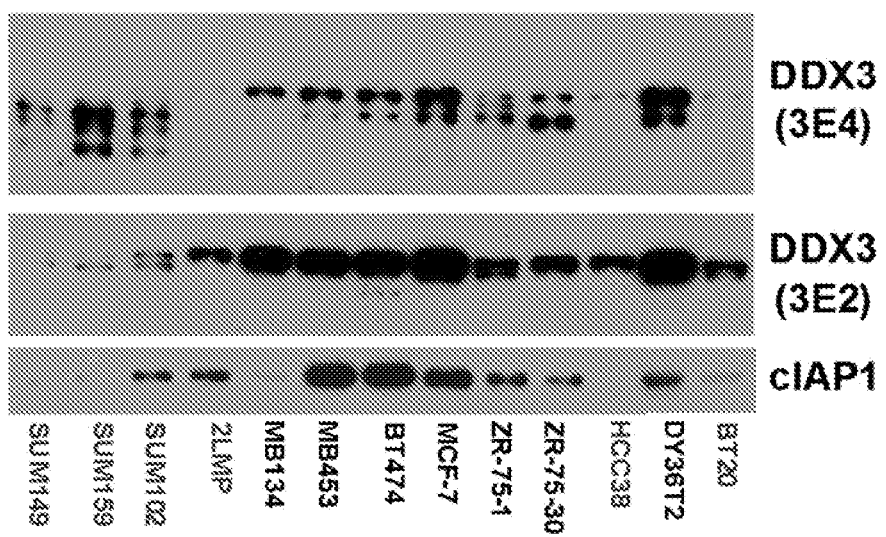

As illustrated in FIG. 6B, in some of the anti-DR5 sensitive cell lines, the MW of DDX3 co-immunoprecipitated with DR5 was smaller as demonstrated by the anti-C-terminal DDX3 antibody, 3E4. This was due to a loss of the N-terminal CARD domain as determined by the N-terminal CARD specific anti-DDX3 antibody, 3E2. Corresponding to the loss of CARD, the cIAP1 was also decreased.

Example 6

Differential Expression of DDX3/IAP Complex in Breast Cancer Stem Cells

Figure 7:
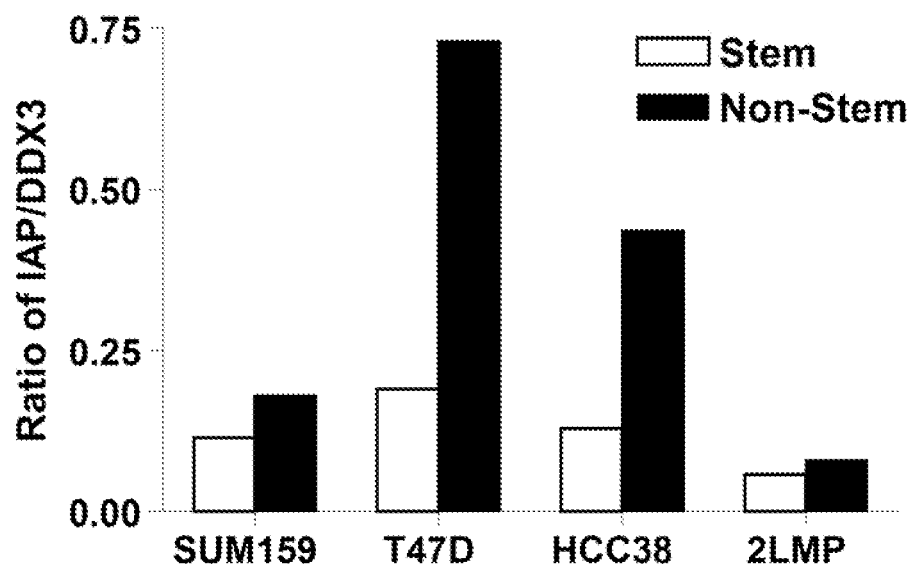
FIG. 7 is a graph showing the ratio of IAP to DDX3 in the DDX3/IAP protein complex in ALDH+/CD44+/CD24− breast cancer stem cells and Aldefluor-non-stem cells.
Figure 8:
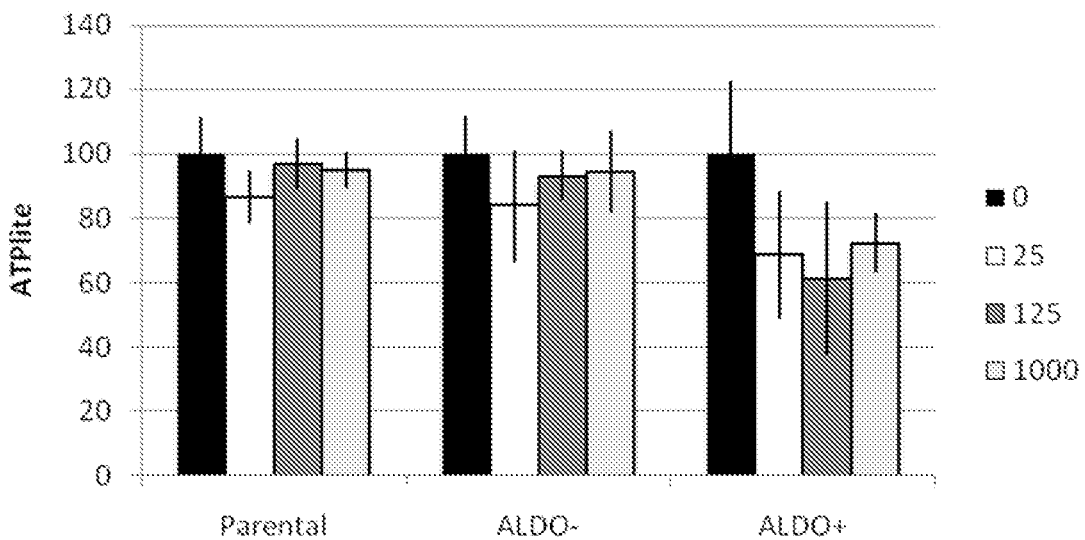
FIG. 8 is a graph showing TRA-8 kills cancer stem cells isolated from TRA-8 resistant cell line, T-47D.
Figure 9:
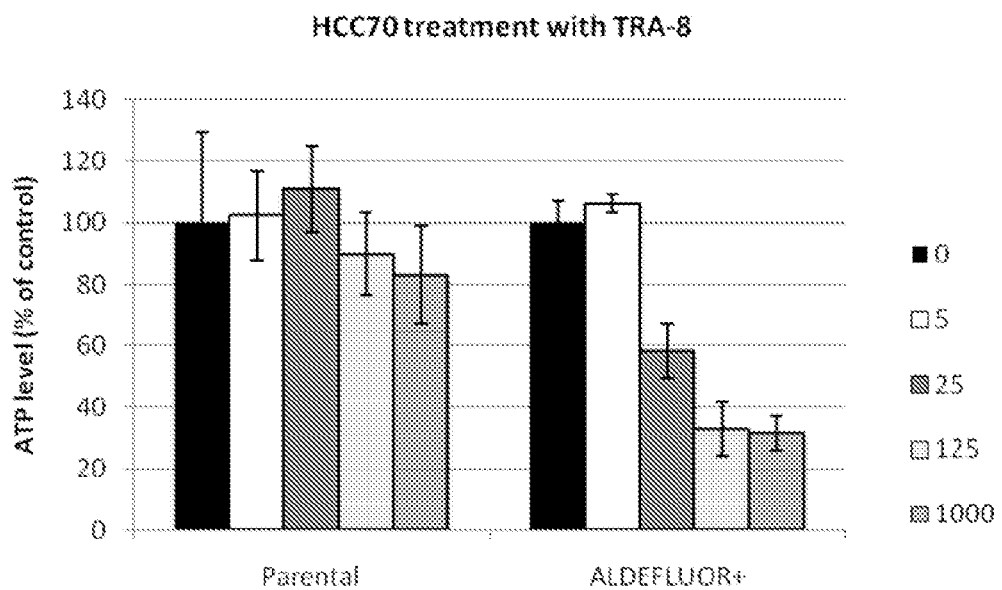
FIG. 9 is a graph showing TRA-8 kills cancer stem cells isolated from TRA-8 resistant cell line, HCC70.
Figure 10:
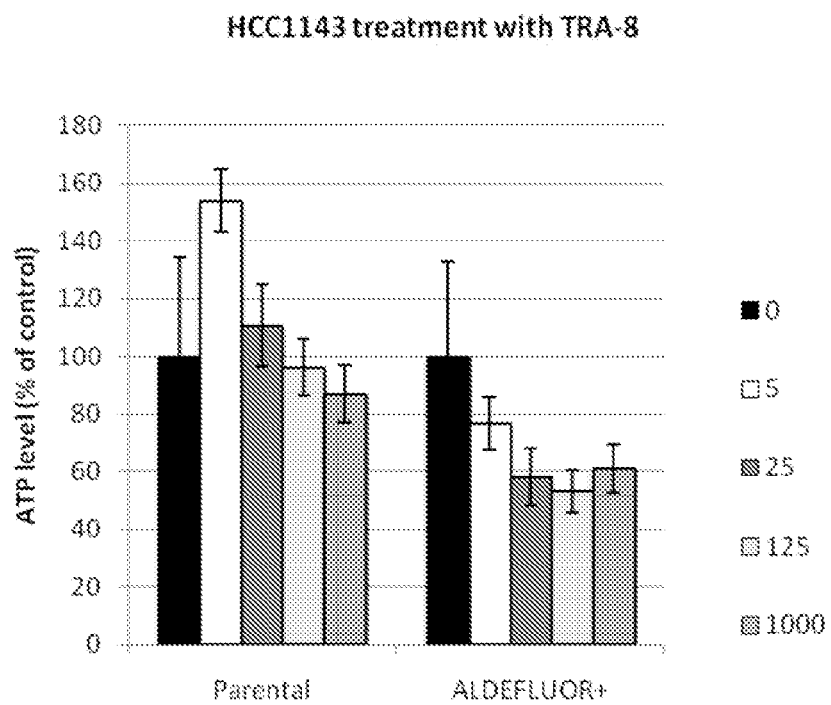
FIG. 10 is a graph showing TRA-8 kills cancer stem cells isolated from TRA-8 resistant cell line, HCC1143.
Figure 11:
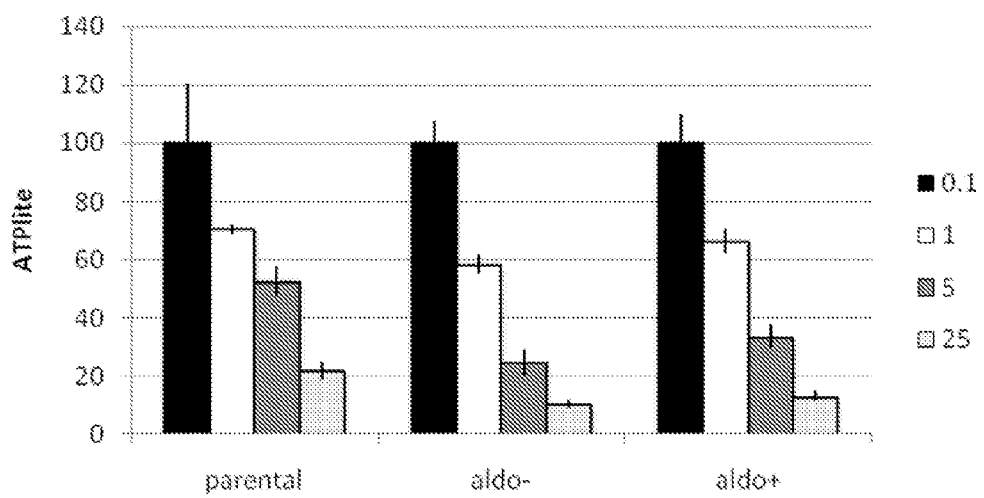
FIG. 11 is a graph showing TRA-8 kills cancer stem cells isolated from TRA-8 sensitive cell line, MB-436.

To determine whether breast cancer stem cells express a different pattern of the DDX3/IAP complex from differentiated cells, the ALDH+/CD44+/CD24− stem cell population was isolated from the non-stem cell population by FACS sorting. Total cell lysate was prepared from about 200,000 sorted cells. The full-length of DDX3 was measured by 3E4 (C-terminus of DDX3)/3E2 (N-terminus of DDX3) antibody pair, and the DDX3/IAPs complex was measured by 3E4 (DDX3)/3H4 (IAPs) antibody pair. The ratio of the DDX3-associated IAPs versus total cellular DDX3 was calculated. The results are shown in FIG. 7. In the TRA-8 sensitive cell lines (SUM159 and 2LMP), stem cell DDX3 complex is low, similar to the non-stem cell component. The TRA-8 resistant cell line (T47D) appears to have a stem cell component with a much lower DDX3 complex than its non-stem cell component.

Example 7

Sensitivity of Cancer Stem Cell Lines to Anti-DR5 (TRA-8) Mediated Cytotoxicity

Figure 12:
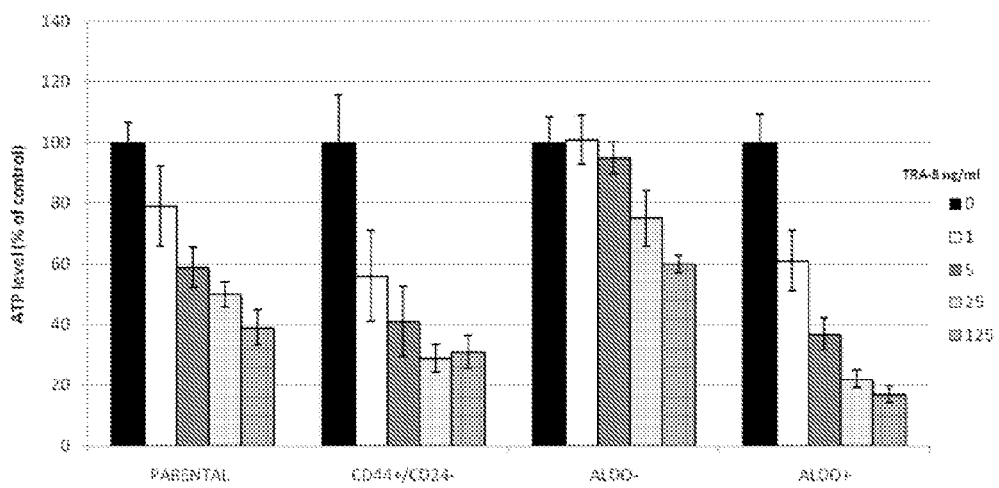
FIG. 12 is a graph showing TRA-8 kills cancer stem cells isolated from TRA-8 sensitive cell line, BT-549.

The ALDH positive (ALDH) and negative (ALDO−) cell populations were isolated from five breast cancer cell lines, T-47D (FIG. 8), HCC70 (FIG. 9), HCC1143 (FIG. 10), MB-436 (FIG. 11) and BT-549 (FIG. 12), which were not sensitive to anti-DR5 mediated cytotoxicity. A $CD44^+/CD24^-$ cell population was also isolated from the BT-549 cell line as shown in FIG. 12. As illustrated in FIGS. 8-12, the ALDH positive subpopulations varied from the original cell line population and exhibited sensitivity to anti-DR5 mediated cytotoxicity. Thus, cancer stem cells (CSCs) are very sensitive to anti-DR5 mediated cytotoxicity even when the CSCs are isolated from cancer cell lines resistant to anti-DR5 mediated cytotoxicity.

Example 8

TRA-8 Induces Apoptosis in Breast Cancer Stem Cell (BCSC) Subpopulations, Blocks Tumorsphere Formation, and Inhibits Tumor Initiation in NOD/SCID Mice $ALDH^+/CD44^+$ $CD24^-$ or $ALDH^+$ only populations were isolated from 10 basal-like breast cancer cell lines that were highly sensitive to TRA-8 mediated cytotoxicity. BCSC subpopulations were found to be varied from 2-16% of the parental populations and exhibited comparable sensitivity to anti-DR5 mediated cytotoxicity (Table 5).

TABLE 5

ALDH+/CD44+CD24− or ALDH+ sorted from basal lines are highly sensitive to TRA-8 mediated cytotoxicity. Cell viability was measured at 24 hours by measuring ATP levels. $IC_{50}$ were calculated by using the Hill equation for at least three experiments run in quadruplicate.

| Phenotype | Cell Line | ALDH+/CD44+ CD24− | Sorted $IC_{50}$ TRA-8 (ng/ml) | Parental $IC_{50}$ TRA-8 (ng/ml) |
|---|---|---|---|---|
| Basal B | SUM 149 | 7% | 0.2 | 1.2 |
|  | HCC38 | 16% | 0.1 | 0.4 |
|  | 2LMP | 5% | 3.1 | 1.9 |
|  | SUM159 | 3% | 0.2 | 0.5 |
|  | MDA-MB436 | 6% | 1.7 | 2.1 |
|  | BT-549 | 2% | 0.4 | 4.0 |
| Basal A | HCC1187 | 2% | 3.6 | 30.6 |
|  | BT20 | 2% | 1.1 | 0.9 |
|  | HCC70 | 8% | 90.2 | >1000 |
|  | HCC1143 | 7% | 24.9 | 298.1 |
| Luminal | T47D | ND | >1000 | >1000 |
|  | DY36T2 | ND | >1000 | >1000 |

Figure 13A:
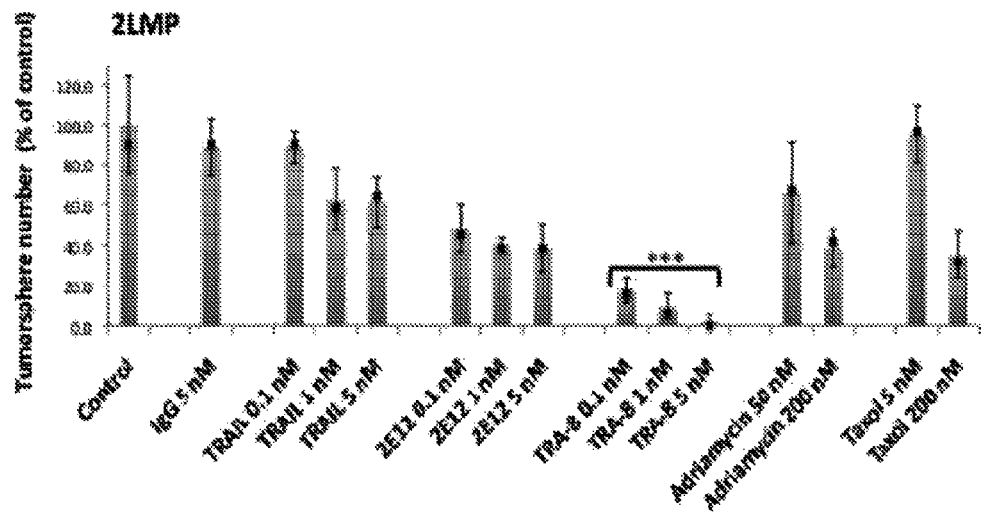
FIGS. 13A and 13B are graphs showing treatment of 2LMP or SUM159 sphere cells with TRA-8 significantly inhibited secondary tumorsphere formation. Bars are normalized relative to untreated control and represent quadruplicate runs. Error bars denote standard deviation (SD).
Figure 13B:
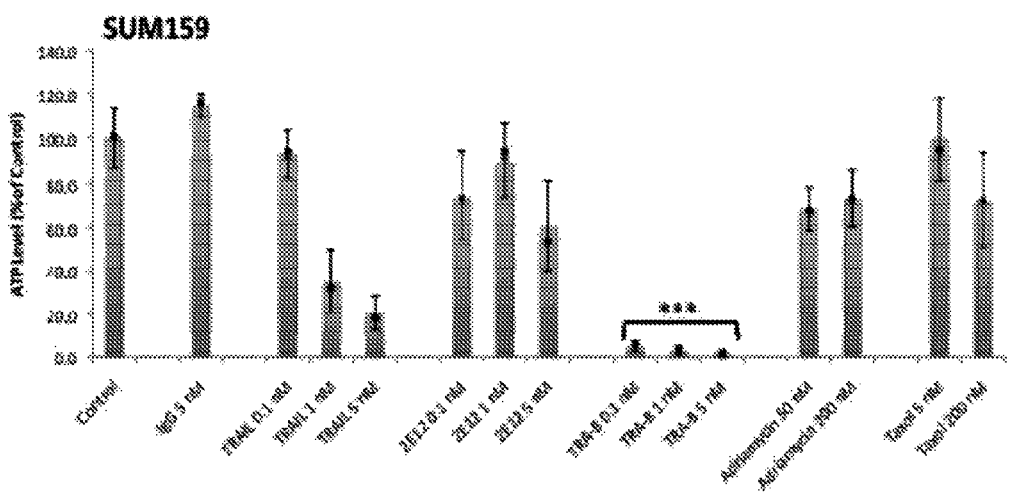

Next, the effects of TRA-8 on sphere formation were investigated. Secondary tumorsphere inhibition was used as a second model for determining BCSC sensitivity to TRA-8, TRAIL, and drug treatment. 2LMP and SUM159 cell lines were sorted for ALDH+ populations. Primary tumorspheres were allowed to form in 3-4 day non-adherent serum free culture conditions. Tumorspheres were mechanically and enzymatically dissociated, plated as single cells in low attachment 96-well plates and treated with IgG control, TRA-8, 2E 12, TRAIL, Adriamycin, and Taxol at increasing concentrations. Secondary tumorsphere formation was greater than 90% inhibited by TRA-8 treatment (p<0.001) (FIGS. 13A and 13B). TRAIL and 2E12, an agonistic anti-DR4 antibody, were only partially inhibitory at equimolar concentrations (FIGS. 13A and 13B). Adriamycin and Taxol did not completely inhibit secondary tumorsphere formation, which is consistent with the published information on chemoresistance of tumorspheres.

Figure 14A:
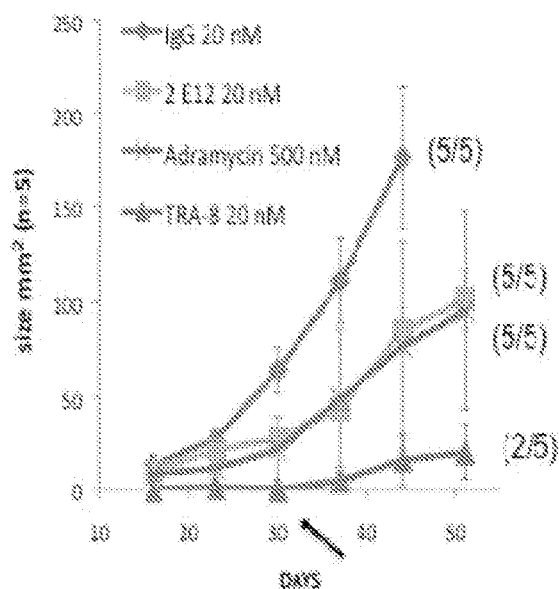
FIGS. 14A and 14B are graphs showing ex vivo treatment of sorted BCSCs inhibited tumorigenesis and progression in NOD/SCID mice. The graphs represent average tumor size (product of two diameters). Two out of five mice developed tumors with TRA-8 treated cells for the 2LMP sorted cells. Five out of five mice developed tumors in the IgG, 2E12, and Adriamycin treated cells for the 2LMP sorted cells administered to mice (FIG. 14A). No tumors developed in TRA-8 treated cells for the sorted SUM159 cells, while five out of five mice developed tumors with IgG treatment of sorted cells, three out of five with 2E12 treatment, and zero out of five with Adriamycin treatment (FIG. 14B).
Figure 14B:
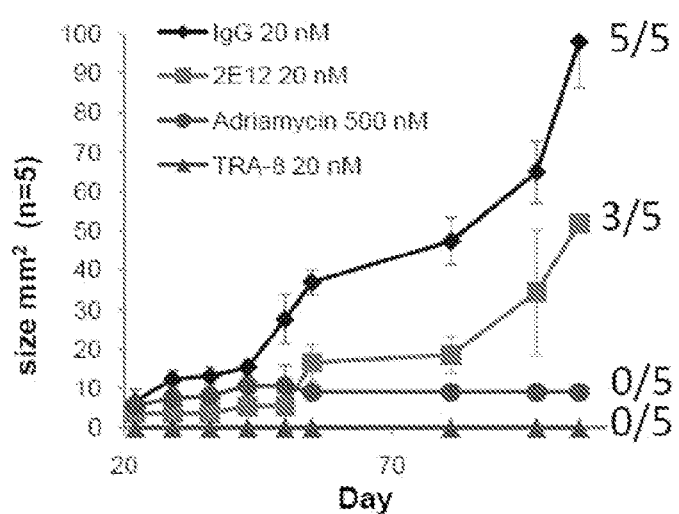

The effects of TRA-8 on the tumorigenicity of ALDH+ cells was next examined. To evaluate the ex vivo therapeutic efficacy of TRA-8, 2LMP and SUM159 cells were sorted for ALDH+ cells by flow cytometry and allowed to recover for 13 hours before treatment with 20 nM TRA-8, 2E12, IgG1 and 500 nM Adriamycin. The cells were treated 3 hours. Then $4 \times 10^4$ cells were mixed 50:50 with Matrigel™ and implanted into the mammary fat pad of NOD/SCID mice. Five of five mice implanted with control IgG treated 2LMP ALDH+ cells were euthanized at 44 days. All five mice showed tumor growth at 44 days (average tumor size exceeded 175 mm²). By day 51, five of five mice with 2E12 treated cells, five of five mice with Adriamycin treated cells, and two of five mice with TRA-8 treated cells developed 2LMP tumors (FIG. 14A) Similar results were obtained with ex vivo treatment of SUM159 ALDH+ cells (FIG. 14B). This study indicates that ex vivo treatment with the anti-DR5 TRA-8 killed BCSCs and inhibited tumor formation and progression.

Figure 15:
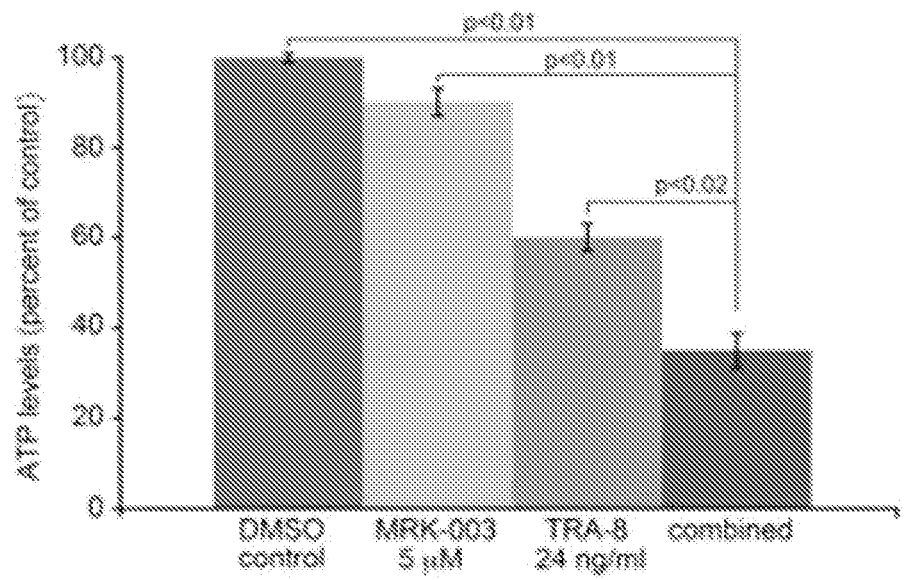
FIG. 15 is a graph showing that MRK003 γ-secretase inhibitor (GSI) and TRA-8 combined were more effective at killing ALDH+ sorted 2LMP cells than either treatment alone. Bars are normalized relative to DMSO-treated controls and represent quadruplicate samples. Error bars denote the standard error of the mean (SEM), and p-values were calculated using a T-test.

Example 9

γ-Secretase Inhibitors (GSIs) and TRA-8 Work Synergistically In Vitro to Kill Basal Type BSCSs 2LMP ALDH+ cells were sorted by flow cytometry and treated with MRK003 GSI (or DMSO) for 24 hours followed by TRA-8 (or media) for an additional 24 hours before measuring ATP levels. The results demonstrated the combination of MRK003 GSI and TRA-8 was more effective in inducing cytotoxicity than either treatment alone (FIG. 15). Similar results were found in studies using CSC-enriched cell populations derived from sphere cultures. The results were confirmed using annexin V-propidium iodide assays and flow cytometry to measure apoptosis. The data revealed low levels of apoptosis in control-treated cells (8% annexin V-positive) that increased following treatment with 24 ng/ml TRA-8 (20% annexin-V-positive) or 5 μM MRK003, (36% annexin-V-positive). However, the combined treatment approach was even more effective with 78% annexin-V-positive.

Example 10

GSIs and TRA-8 Inhibit Tumor Growth

Figure 16:
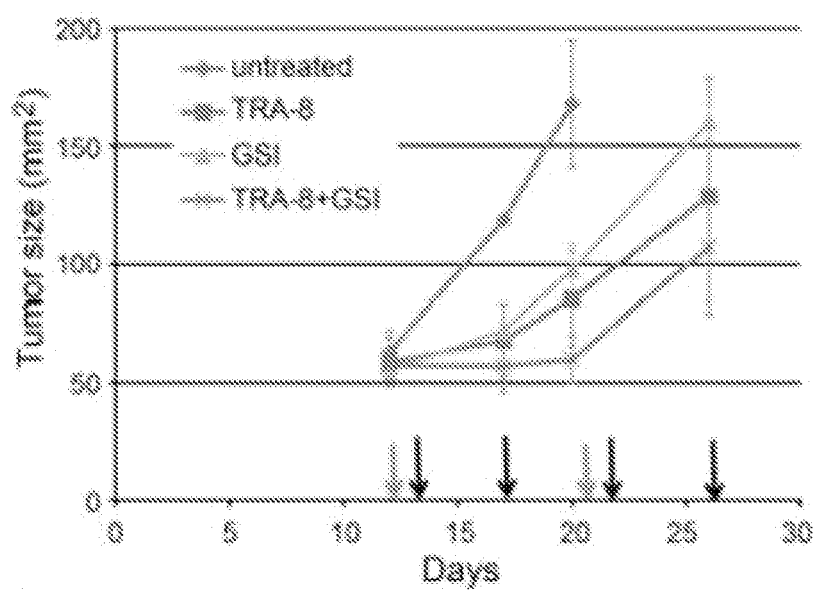
FIG. 16 is a graph showing NOD/SCID mice with established 2LMP tumors treated with MRK003 plus TRA-8 has striking growth inhibition during the first week. NOD/SCID mice were treated with two doses of 300 mg/kg of MRK003 (1 day on, 6 days off) followed by four doses of 48 ng/ml of TRA-8 (1 day on, 3 days off).

The effect of GSI, TRA-8, or both on pre-established tumors in a murine model of breast cancer was examined. 2LMP cells were implanted into the mammary fat pad of 15 NOD/SCID mice and tumors were allowed to develop over 12 days. Twelve animals were randomized into 4 groups of 3 animals each and 300 mg/kg MRK003 administered via gavage (FIG. 16). On days 13 and 17, 200 μg TRA-8 were administered intraperitoneally (FIG. 16), and the treatment regimen repeated starting on day 21. Tumor measurements were taken over time, and the animals treated with TRA-8, GSI, or the combination compared to untreated control. The results with the GCI plus TRA-8 combination show striking growth inhibition at the early time points suggesting that this dual therapeutic approach can be effective.

Example 11

TRA-8 Reduces Notch Activation while Inducing Apoptosis

Figure 17:
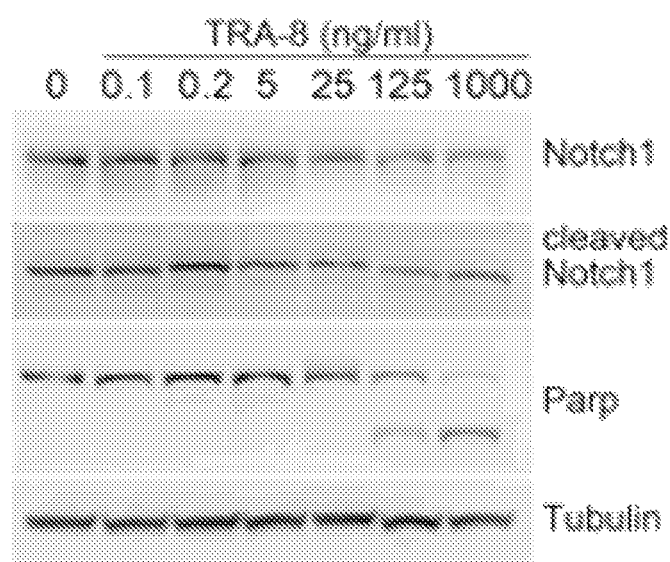
FIG. 17 is an image of a Western blot showing that TRA-8 stimulation of 2LMP cells for 5 hours results in a decrease of Notch 1 receptor expression and cleaved Notch 1 indicating a reduction in Notch 1 activation. This occurred simultaneously with induction of apoptosis (poly ADP ribose polymerase (Parp) cleavage).

To determine if TRA-8 modulated Notch activation, and, thus, might contribute to any synergistic activity identified between TRA-8 and MRK003 GSI, Notch expression and activation were examined using Western blot analysis. FIG. 17 shows that 25 ng/ml TRA-8, which showed detectable Parp cleavage (apoptosis) also demonstrated reduced expression of Notch1 and cleaved Notch1 (the active form of Notch or NICD). Thus, TRA-8 may further reduce Notch activation in breast cancer tumor cells and contribute to the GSI and TRA-8 synergy seen in the experiments presented above.

What is claimed is:

1. A method of killing cancer stem cells in a subject comprising
   (a) determining the level of DR5 agonist resistance or sensitivity of cancer stem cells in a biological sample from the subject comprising the steps of,
      (i) acquiring a biological sample from a subject with cancer, wherein the sample comprises cancer stem cells, and
      (ii) detecting the level of IAP in one or more DR5/DDX3/IAP complexes in an enriched population of cancer stem cells from the sample, a high level of IAP in the enriched population of cancer stem cells indicating sensitivity of the cancer stem cells to a DR5 agonist;
   (b) administering to the subject a therapeutically effective amount of a DR5 agonist, and (c) optionally, administering to the subject an IAP inhibitor, if the cancer stem cells are resistant to the DR5 agonist.

2. The method of claim 1, wherein the DR5 agonist is a DR5 antibody.

3. The method of claim 1, wherein the cancer stem cells are positive for ALDH, CD44, or both ALDH and CD44.

4. The method of claim 1, wherein the biological sample is a tumor biopsy.

5. The method of claim 1, wherein the cancer is breast cancer.

6. The method of claim 5, wherein the breast cancer is triple negative breast cancer.

\* \* \* \* \*

UNITED STATES PATENT AND TRADEMARK OFFICE
CERTIFICATE OF CORRECTION

| | | |
|---|---|---|
| PATENT NO. | : 8,703,712 B2 | Page 1 of 1 |
| APPLICATION NO. | : 13/634401 | |
| DATED | : April 22, 2014 | |
| INVENTOR(S) | : Donald J. Buchsbaum et al. | |

It is certified that error appears in the above-identified patent and that said Letters Patent is hereby corrected as shown below:

On the Title Page

Item (73), Assignee should read as follows:

-- The UAB Research Foundation, Birmingham, AL (US); and

Loyola University Chicago, Maywood, IL (US) --

Insert Item -- (60), Related U.S. Application Data -- to read as follows:

-- Provisional application No. 61/315,143, filed March 18, 2010. --

Signed and Sealed this
Fifth Day of August, 2014

Michelle K. Lee
*Deputy Director of the United States Patent and Trademark Office*